(12) United States Patent
Gore et al.

(10) Patent No.: US 8,269,627 B2
(45) Date of Patent: Sep. 18, 2012

(54) STATUS MONITORING SYSTEM FOR A FENESTRATION UNIT

(75) Inventors: Sachin Gore, Stillwater, MN (US); David Plummer, Hudson, WI (US); Daniel Timmerman, Hudson, WI (US)

(73) Assignee: Andersen Corporation, Bayport, MN (US)

( * ) Notice: Subject to any disclaimer, the term of this patent is extended or adjusted under 35 U.S.C. 154(b) by 419 days.

(21) Appl. No.: 12/323,542

(22) Filed: Nov. 26, 2008

(65) Prior Publication Data

US 2009/0140858 A1 Jun. 4, 2009

Related U.S. Application Data

(60) Provisional application No. 60/991,459, filed on Nov. 30, 2007.

(51) Int. Cl.
 *G08B 13/08* (2006.01)
(52) U.S. Cl. .......... 340/547; 340/545.6; 340/545.7; 340/545.8; 340/545.9; 340/539.13; 340/539.26; 340/541; 340/542; 292/240; 292/241
(58) Field of Classification Search .......... 340/547, 340/545.6, 545.7, 545.8, 545.9, 539.1, 539.26, 340/542, 539.13, 541; 292/241, 240
See application file for complete search history.

(56) References Cited

U.S. PATENT DOCUMENTS

| | | |
|---|---|---|
| 3,525,830 A | 8/1970 | Hawkins |
| 3,641,540 A | 2/1972 | Cutler et al. |
| 4,196,422 A | 4/1980 | Swigert et al. |
| 4,346,372 A | 8/1982 | Sandberg |
| 4,360,803 A | 11/1982 | Heiland |
| 4,381,504 A | 4/1983 | Bitko |
| 4,465,997 A | 8/1984 | Hines |
| 4,755,799 A | 7/1988 | Romano |
| 4,760,380 A | 7/1988 | Quenneville et al. |
| 4,845,471 A | 7/1989 | Chu |
| 5,006,766 A | 4/1991 | Yuhas et al. |
| 5,077,547 A * | 12/1991 | Burgmann ............. 340/501 |
| 5,226,256 A | 7/1993 | Fries et al. |
| 5,311,168 A | 5/1994 | Pease, Jr. et al. |
| 5,355,059 A | 10/1994 | McMillan |
| 5,449,987 A | 9/1995 | McMillan |
| 5,479,151 A | 12/1995 | Lavelle et al. |
| 5,486,812 A * | 1/1996 | Todd ................. 340/539.14 |
| 5,499,014 A | 3/1996 | Greenwaldt |
| 5,595,075 A * | 1/1997 | Chen ......................... 70/95 |
| 5,686,890 A | 11/1997 | Ko |
| 5,712,621 A * | 1/1998 | Andersen ............... 340/547 |
| 5,783,995 A | 7/1998 | Jackson |
| 5,841,361 A | 11/1998 | Hoffman |
| 5,999,095 A | 12/1999 | Earl et al. |
| 6,057,769 A | 5/2000 | Stevenson |
| 6,078,269 A | 6/2000 | Markwell et al. |
| 6,212,923 B1 | 4/2001 | Clark |
| 6,420,973 B2 | 7/2002 | Acevedo |
| 6,441,735 B1 | 8/2002 | Marko et al. |

(Continued)

*Primary Examiner* — Tai T Nguyen
(74) *Attorney, Agent, or Firm* — Womble, Carlyle, Sandridge & Rice, LLP

(57) ABSTRACT

A status monitoring device for a fenestration unit is provided. The device is positioned in or on the fenestration unit and includes a panel position sensor and a lock status sensor. The device is capable of transmitting panel position data and lock status data to a remote device, trigger an audible alarm on the device or the remote device, trigger a visual alarm on the device or the remote device, or a combination of these.

84 Claims, 14 Drawing Sheets

U.S. PATENT DOCUMENTS

| | | |
|---|---|---|
| 6,615,629 B2 | 9/2003 | Bates et al. |
| 6,661,340 B1 | 12/2003 | Saylor et al. |
| 6,724,316 B2 * | 4/2004 | Addy et al. ............... 340/686.1 |
| 6,778,086 B2 | 8/2004 | Morrone et al. |
| 6,853,145 B2 * | 2/2005 | Kang et al. ............... 315/169.1 |
| 6,871,885 B2 * | 3/2005 | Goldenberg et al. ......... 292/241 |
| 6,888,459 B2 | 5/2005 | Stilp |
| 6,963,280 B2 | 11/2005 | Eskildsen |
| 6,968,646 B2 * | 11/2005 | Goldenberg et al. ........... 49/181 |
| 6,987,450 B2 | 1/2006 | Marino et al. |
| 7,019,639 B2 | 3/2006 | Stilp |
| 7,023,341 B2 | 4/2006 | Stilp |
| 7,042,353 B2 | 5/2006 | Stilp |
| 7,053,764 B2 | 5/2006 | Stilp |
| 7,057,512 B2 | 6/2006 | Stilp |
| 7,068,162 B2 * | 6/2006 | Maple et al. ............ 340/539.11 |
| 7,079,020 B2 | 7/2006 | Stilp |
| 7,079,034 B2 | 7/2006 | Stilp |
| 7,084,756 B2 | 8/2006 | Stilp |
| 7,091,827 B2 | 8/2006 | Stilp |
| 7,119,658 B2 | 10/2006 | Stilp |
| 7,119,678 B2 | 10/2006 | Katz |
| 7,120,795 B2 | 10/2006 | Raphael et al. |
| 7,142,111 B2 | 11/2006 | Eskildsen et al. |
| D534,146 S | 12/2006 | Stilp et al. |
| 7,147,255 B2 * | 12/2006 | Goldenberg et al. ......... 292/241 |
| D534,519 S | 1/2007 | Stilp et al. |
| 7,158,029 B1 | 1/2007 | Martyn |
| 7,202,789 B1 | 4/2007 | Stilp |
| 7,227,463 B2 | 6/2007 | Merrell |
| 7,230,532 B2 | 6/2007 | Albsmeier et al. |
| 7,355,515 B2 | 4/2008 | Lee et al. |
| 2007/0194914 A1 * | 8/2007 | Gates ............................ 340/541 |

* cited by examiner

STATUS MONITORING SYSTEM FOR A FENESTRATION UNIT

CROSS-REFERENCE TO RELATED APPLICATION

This application claims benefit of U.S. Provisional Application No. 60/991,459, filed Nov. 30, 2007, which is hereby incorporated by reference in its entirety.

BACKGROUND

Building security systems can vary in complexity from simple burglar alarms triggered by breakage of windows or other fenestration members, to comprehensive intrusion detection systems that collect data from video cameras, laser beams, infrared sensors, microphones, etc., analyze the data, and communicate information to a variety of destinations, such as security stations and automated building control centers. While complex and relatively expensive security systems are useful, applications such as residential housing need a simpler, lower cost monitoring system capable of collecting multiple types of security related data and transmitting data to one or more locations for analysis and/or action. The system's data collecting and transmitting components should also be self contained and self powered, possess wireless communication capability, and be relatively simple to install in both new and existing structures.

SUMMARY

In one embodiment, a fenestration unit is provided that includes a frame, at least one panel disposed in the frame with the panel being movable between a closed position and an open position, and a locking member having a locked position, for locking the panel in the closed position, and an unlocked position for allowing the panel to be opened. A first sensor is included to detect when the panel is in the closed position and when the panel is in the open position and a second sensor is included to detect when the latch is in the locked position and when the latch is in the unlocked position. A processor coupled to the first sensor and the second sensor is also included, with the processor being programmed to determine a status of the fenestration unit based at least on the detections of the sensors. Optionally, this embodiment can include a transmitter for transmitting the status of the fenestration unit to a remote location. Further, either the first sensor or the second sensor can include a reed switch and an associated magnet, or can include a mechanical switch. The fenestration unit in this embodiment can be a window, or can be a door. Further still, an indicator can be included on the fenestration unit that indicates the status of the fenestration unit, and the indicator can be an audible signal generator or can be a light source.

In another embodiment, a status monitoring device for a fenestration unit is provided that includes at least a first panel and a second panel movable with respect to the first panel. The device in this embodiment includes a switch on the first panel, and a switch triggering component on the second panel. The device transmits a first signal when the switch is in a first position proximate the triggering component and transmits a second signal when the switch is in a second position not proximate the triggering component. For example, the first position could be parallel the magnet and the second position could be non-parallel the magnet. Optionally, the switch of the device is adjacent a latch. Optionally still, the device can include a visible light signal output device that indicates whether the switch is in the first position or the second position. Further, the device can include an audible output device that provides an audible alarm when the switch is moved from the first position. Further still, the device can include a position sensor that triggers an alarm when the switch is moved from the first position. In this embodiment, the fenestration unit can be a window and the device can be integral the window. Alternatively, the fenestration unit can be a door adjacent a wall and the device can be part of a slide bar lock moveable between the door and the wall. The switch can be a magnetically operated reed switch, and the triggering component can be a magnet.

In another embodiment, a status monitoring device is installed adjacent a lock that includes a latch and a keeper. The device in this embodiment includes a first housing disposed adjacent the latch, a second housing disposed adjacent the keeper, a switch disposed in the first housing or in the second housing, a switch triggering component disposed in the first housing or in the second housing, and a transmitter for communicating the position of the latch with respect to the keeper to a remote location. Optionally, the switch triggering component can be a magnet. Optionally still, the device can include a visible light signal output indicating whether the switch is in the first position or the second position. Further, the device can include an audible output device capable of providing an audible alarm when the latch is moved with respect to the keeper or when other predetermined events occur. Further still, the device can include a position sensor that triggers an alarm when the latch is moved from the keeper. The device of this embodiment can be installed under the lock, and a reed switch can be installed adjacent the lock.

In another embodiment, a status monitoring system for a closure assembly is provided. The system includes a locking member position sensor, a closure panel position sensor, a status code generator, and a status code transmitter. In this embodiment, the locking member position sensor, the closure panel position sensor, the status code generator, and the status code transmitter are integrated into a single unitary device, which is positioned to sense the position of a locking member and the position of a closure panel. The status code generator in this embodiment generates a status code based upon both locking member position and closure panel position. Further, a status code receiver and an output device can be provided. Further still, the locking member position sensor can be a magnetically operated reed switch, a mechanically operated switch, an acoustical sensor, Radio Frequency Identification (RFID) device, or an optical sensor. Optionally, the closure position sensor can be a magnetically operated reed switch, a mechanically operated switch, an acoustical sensor, an RFID device, or an optical sensor. In this embodiment, a battery can be contained within the unit, with the battery being held in a battery carrier movable from a position interior the unit to a position exterior the unit.

In another embodiment, a status monitoring system for a closure assembly is provided. The closure assembly includes a fixed frame holding a panel moveable from a closed position to an open position, and a locking member for holding the panel in the closed position. The system includes a monitoring device that includes a locking member position sensor, a closure panel position sensor, a microprocessor, and a status code transmitter. The locking member position sensor, the closure panel position sensor, the microprocessor, and the status code transmitter operate in an electronically integrated manner. The monitoring device is positioned to sense both the position of the locking member and the position of the closure panel. The microprocessor generates a status code that integrates the locking member status with closure panel position.

Generally, the system includes a status code receiver. Optionally, the system includes an output device. The locking member position sensor generally is a magnetically operated reed switch, a mechanically operated switch, an acoustical sensor, RFID device, or an optical sensor. Further, the closure position sensor is a magnetically operated reed switch, a mechanically operated switch, an acoustical sensor, an RFID device, or an optical sensor. The system can also include a battery contained within the monitoring device. The battery can be held in a battery carrier movable from a position interior the unit to a position exterior the unit.

The device of this invention generally provides a status monitoring that is coupled to or interfaces with a fenestration unit, its components, and its surrounding environs. Such a device may be incorporated, for example, in the latch mechanism of a double hung window unit or the strike plate of a door. The information collected or received by the device can include various status reports of the fenestration unit itself such as whether the fenestration unit is open or closed. The device can gather information from the fenestration units components such as locks to detect whether the lock is locked or unlocked, or can collect information about the environment surrounding the fenestration unit, such as outside or inside temperature, humidity, moisture, light, motion, etc. Also, the device can gather information such as the time of a change in the position of the fenestration unit, the position of the lock, or an interior or exterior environment.

The information gathered can be recorded or processed locally by the device, can be locally output via a light, alarm, or other visual or audible source, and/or can be exported to another unit, such as via a wired or wireless link to a central information unit with storage or command capabilities, where further processing can be performed. Such further processing can include transmitting a message to an alarm monitoring system or notifying authorities and/or the occupants of a building of a triggering event. The central information unit can collect and store information either from a single status monitoring device, or can collect information from multiple monitoring devices.

The status monitoring device can communicate a condition of the fenestration unit or its surroundings to the occupant of the room via light, sound, or the like. Based on information sensed by the device or information provided to the device (from another source), the device can communicate to the occupant, such as through a series of light flashes or audible beeps. For example, if a smoke detector in a building senses a fire or smoke, a signal can be sent to status monitoring devices on the windows and/or doors. The devices can then trigger flashing lights, audible beeps, or the like, which can act as a beacon, indicating an exit route out of the building. The device lights or beepers can also flash or sound to indicate a tripped security alarm in the building or a weather alert in the area where the building is located.

In some embodiments, the status monitoring device can either be installed on an existing fenestration unit, such as under existing hardware, such as a latch assembly, or can be installed during manufacture of a new fenestration unit. The device can be utilized on all types of fenestration units (windows and doors), for example, including casement, awning, roof window, double hung, single hung, gliding, hinged patio doors, sliding patio doors, entry doors, and garage doors.

The device can interface with a fenestration unit as well as its hardware and surroundings, can detect the condition of the hardware as well as the venting status of the fenestration unit, and can, for example, enable a builder or contractor to monitor the windows and doors during construction to provide a level of security or awareness on the jobsite during building construction.

DETAILED DESCRIPTION

Figure 1:
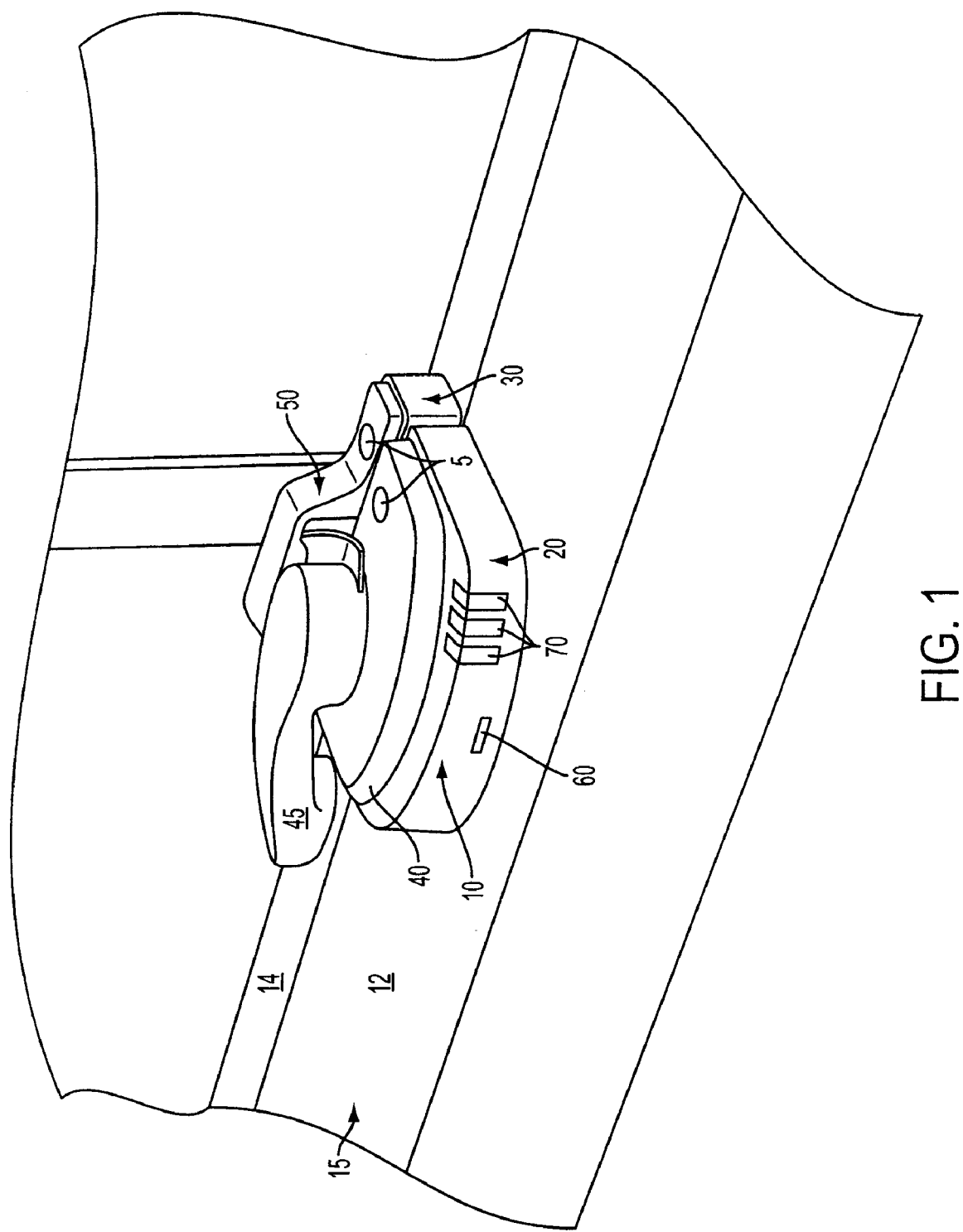
FIG. 1 shows a first embodiment of a status monitoring device under a traditional latch on a fenestration unit.

For a more complete understanding of the present invention, reference will be made to the following detailed description and accompanying drawings, wherein like reference numerals designate corresponding parts throughout the figures.

To facilitate an understanding and explanation of the invention, the elements and numerals as described herein may be referred to with the terms "upper," "lower," "top," "bottom," "front," and "back" to distinguish portions of the device. These conventions are merely included for ease of explanation and understanding and should not be construed as limiting in any manner. The descriptions of the parts detailed herein as "upper," "lower," etc. also can be referred to as "first," "second," etc.

FIG. 1 shows a first embodiment of a status monitoring device under a traditional latch on a fenestration unit, with status monitoring device 10 having a first housing 20 under latch element base 40 and second housing 30 under keeper element base 50. The first housing 20 is affixed under latch element base 40 by screws 5 to the top rail or check rail 12 of lower sash of fenestration unit 15 (such as a single or double hung window), while second housing 30 is affixed under keeper 50 by screws 5 to the bottom rail 14 of upper sash of fenestration unit 15. A latch 45 generally is affixed atop latch element base 40 and is capable of being selectively engaged with keeper 50. The status monitoring device 10 is capable of detecting whether the latch 45 is engaged within keeper 50.

Also shown in FIG. 1, status monitoring device 10 can optionally include an indicator light (or lights) 60 and can optionally include an audible output 70, such as a speaker, beeper, or alarm. If a status monitoring device according to FIG. 1 is to be installed on an existing fenestration unit, the lock is first removed from the rails by removing the screws and then reinstalled atop the housings 20 and 30.

Figure 2:
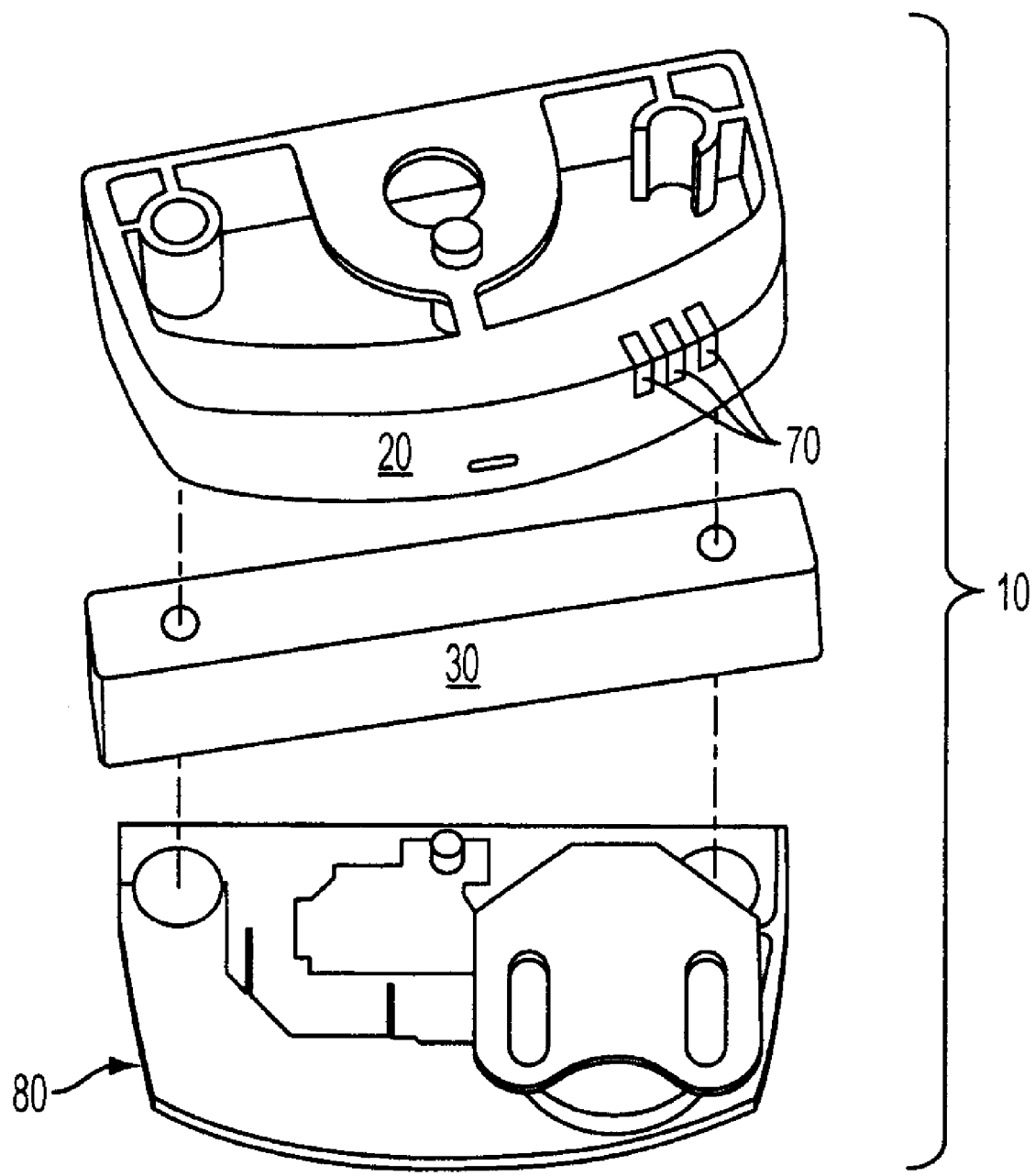
FIG. 2 shows a part view of the first embodiment status monitoring device housing and circuit board.

FIG. 2 shows a part view of the first embodiment of the device 10 including the status monitoring device's first housing 20, second housing 30, and circuit board 80. The circuit board 80 can include a battery, a microprocessor, a transmitting unit, receiving unit, circuitry, sensors, and/or other sensors that collect information.

The status monitoring system discussed herein is not limited to any particular mechanical configuration, but can be utilized to integrate any reliable indication of lock engagement with any reliable indication of panel closure to produce a status code that is wirelessly transmitted to a status code receiver. Further, other types of information, in addition to lock position status and panel position status, can also be sensed and transmitted to status code receiver 110. Installation of monitor unit 50 and spacer 56 can be performed during factory assembly or as a retrofit at any later time.

Figure 3:
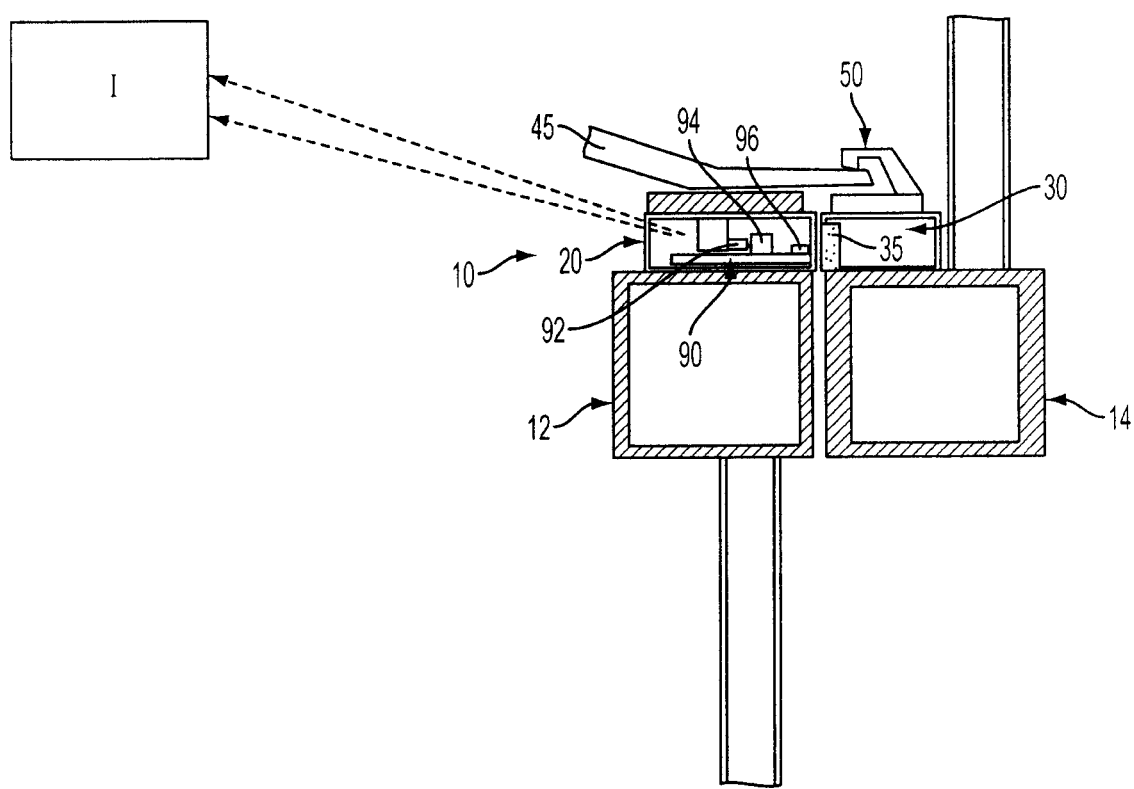
FIG. 3 shows a cut-away view of the status monitoring device of the first embodiment.

FIG. 3 shows a cut-away view of the status monitoring device of the first embodiment in an exemplary configuration. The status monitoring device 10 can be placed outside the sash to allow retrofitting to an existing sash. Referring to FIG. 3, second housing 30 contains a magnet 35 that triggers an indication that trips a reed switch 96 in housing 20 when the window is closed as an indication of a closed window condition. Latch 45 is suitably configured to allow space for a monitor unit 90 with portion 92 for operating lock position switch 94 and magnetically operated reed switch 96. The term lock position switch is used herein in the broad sense of any device, such as an optical or an RFID device, that provides a signal indicative of when lock 45 is moved from the unlocked to the locked position, or from the locked to the unlocked position. The magnetically operated reed switch 96 and magnet 35 cooperate to provide information about the device 10, such as whether the window sashes are separated and thus the window is open.

In place of the described switch 96 and magnet 35, which sense the proximity of first housing 20 to second housing 30, other embodiments can use alternative proximity sensors, which can be based on optical, mechanical, RFID, or other proximity sensitive phenomena.

Figure 4:
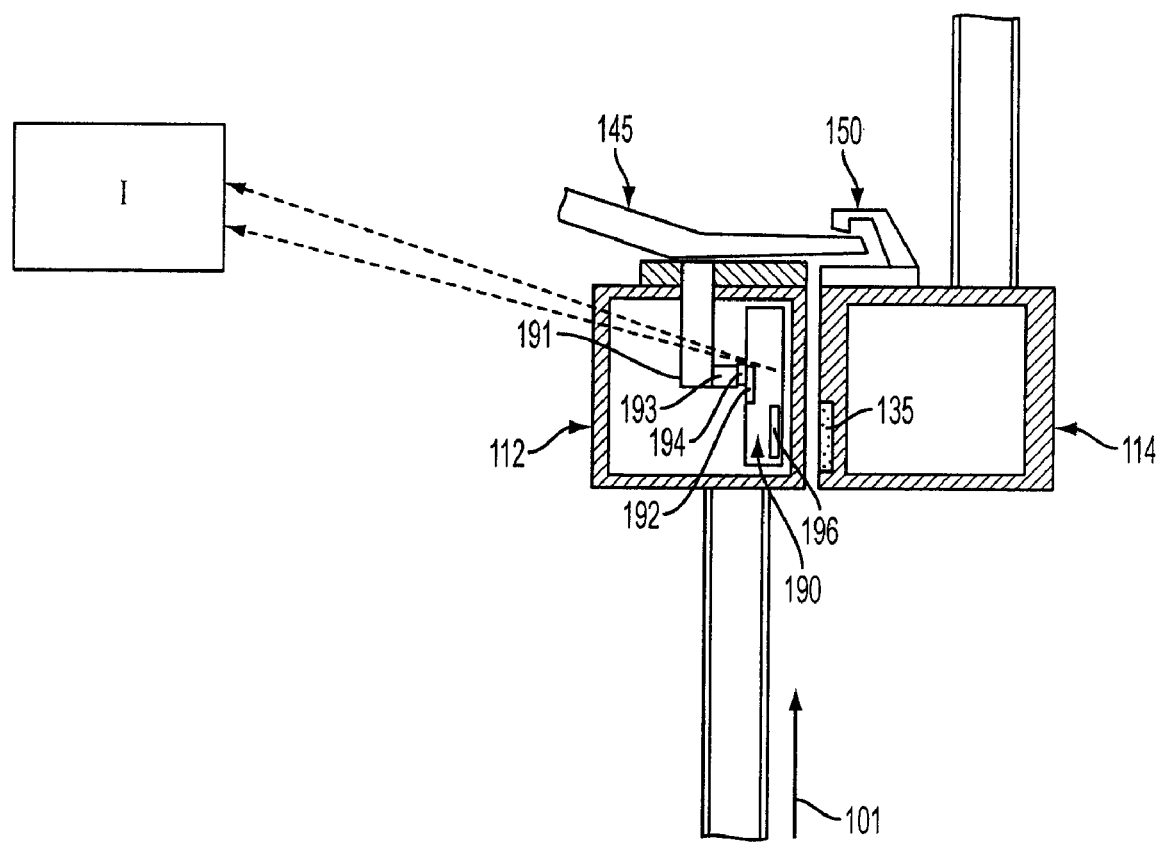
FIG. 4 shows a cut-away view of a status monitoring device of a second embodiment in the rail of the fenestration unit under a traditional latch.

Another common fenestration configuration is that in which one panel slides past another panel. Examples of this configuration include vertically sliding windows, such as single hung or double hung windows, and horizontally sliding windows and doors. FIG. 4 shows a cut-away view of a status monitoring device of a second embodiment built into the rail of the fenestration unit beneath a traditional latch mechanism. Referring to FIG. 4, vertically sliding top rail of lower sash 112, sometimes referred to as the check rail, overlaps or aligns with the lower rail of upper sash 114 when the window is closed, as shown, and the rails moves apart when the window is opened. The upper sash may also be slidable, in which case the overall window unit is called a double hung unit, or it may be fixed, in which case the overall window unit is called a single hung unit. When both sashes are in the closed position, latch 145 can be rotated into engagement with keeper 150 to lock the two sashes together, thereby preventing the opening of either sash.

Monitor unit 190, located in check rail 112, is equipped with magnetically operated reed switch 196 and a mechanical switch 192. Rail 114 is equipped with magnet 135. When both sashes are in the closed position shown in FIG. 4, magnet 135 is in close proximity to reed switch 196, thereby activating it to produce a signal indicative that the sashes are in the closed position. Latch 145 is equipped with projecting finger 193, attached to a shaft 191, which engages or disengages activation portion 194 of switch 192 to activate or deactivate the switch as an indication that the latch has been engaged or disengaged. Activation portion 194 is typically a spring biased lever or button coupled to an electrical switch. Monitor 190 electronically integrates the indications of lock status and sash closure status into an integrated status code or information I that is transmitted to a status code receiver.

Figure 5:
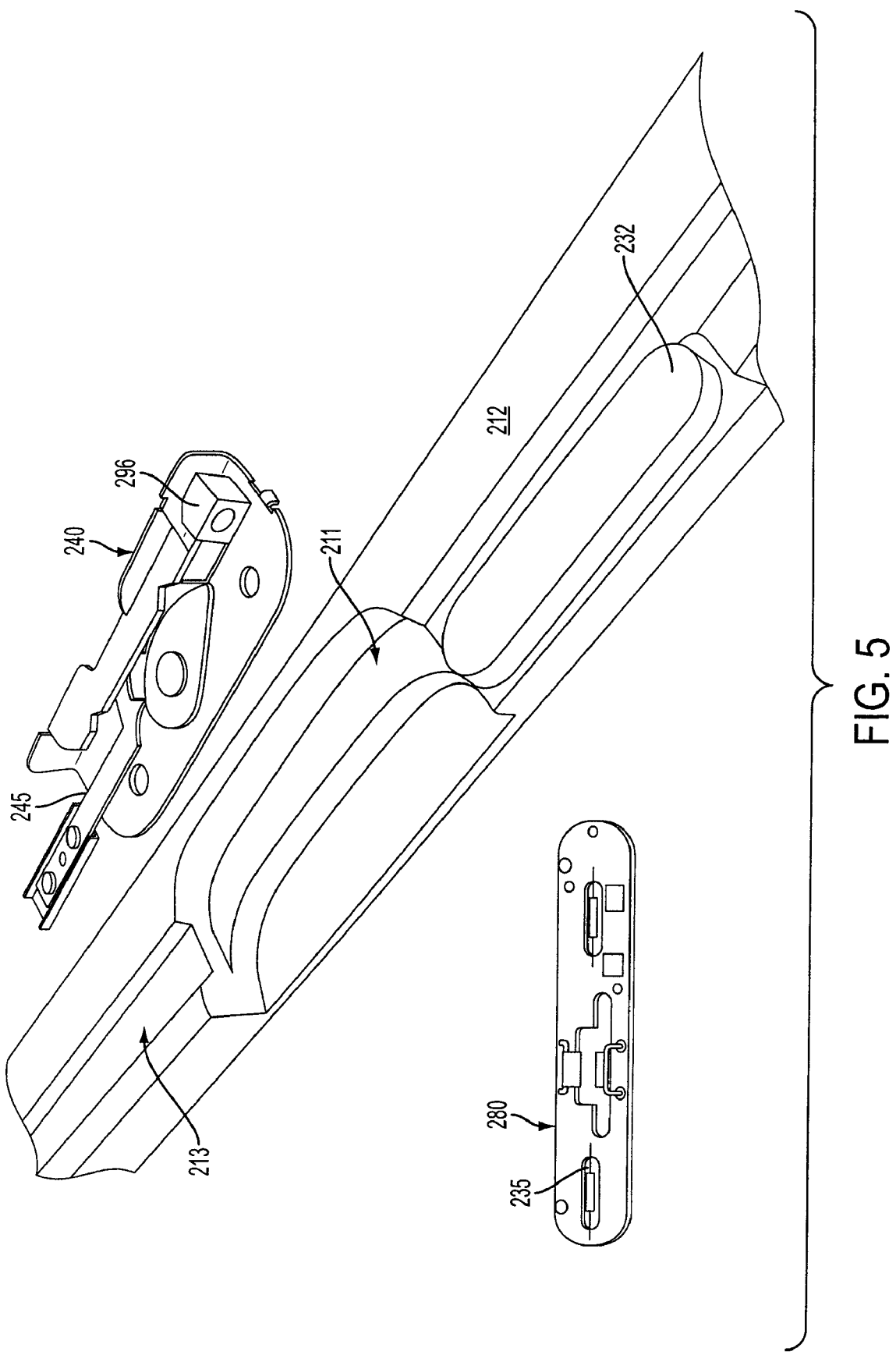
FIG. 5 shows a partially deconstructed view of a status monitoring device of a third embodiment in a rail of a fenestration unit adjacent a sliding-type latch with an integrated magnet.
Figure 6:
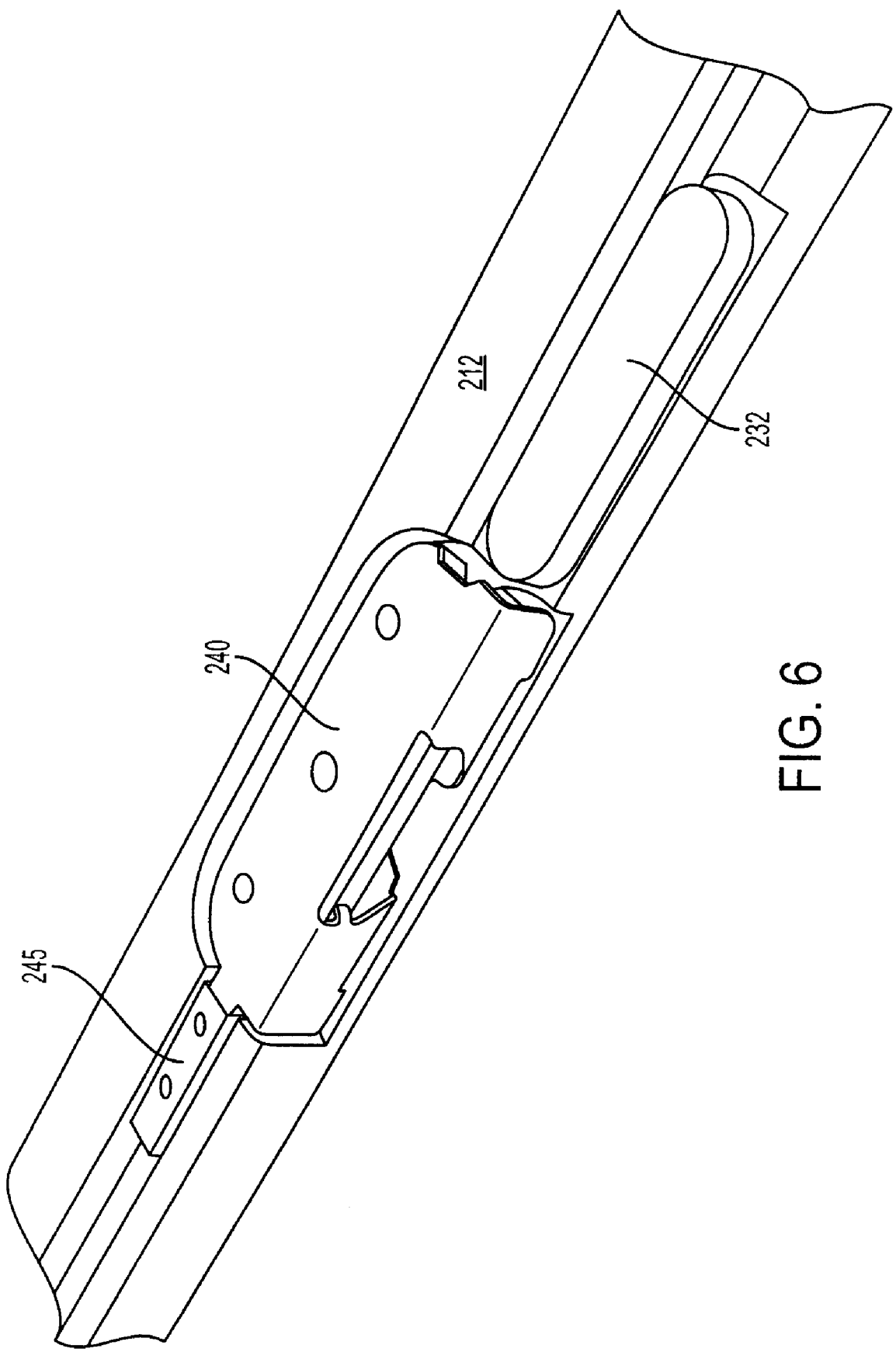
FIG. 6 shows the third embodiment of the status monitoring device of FIG. 5 with the latch in position on the rail.
Figure 7:
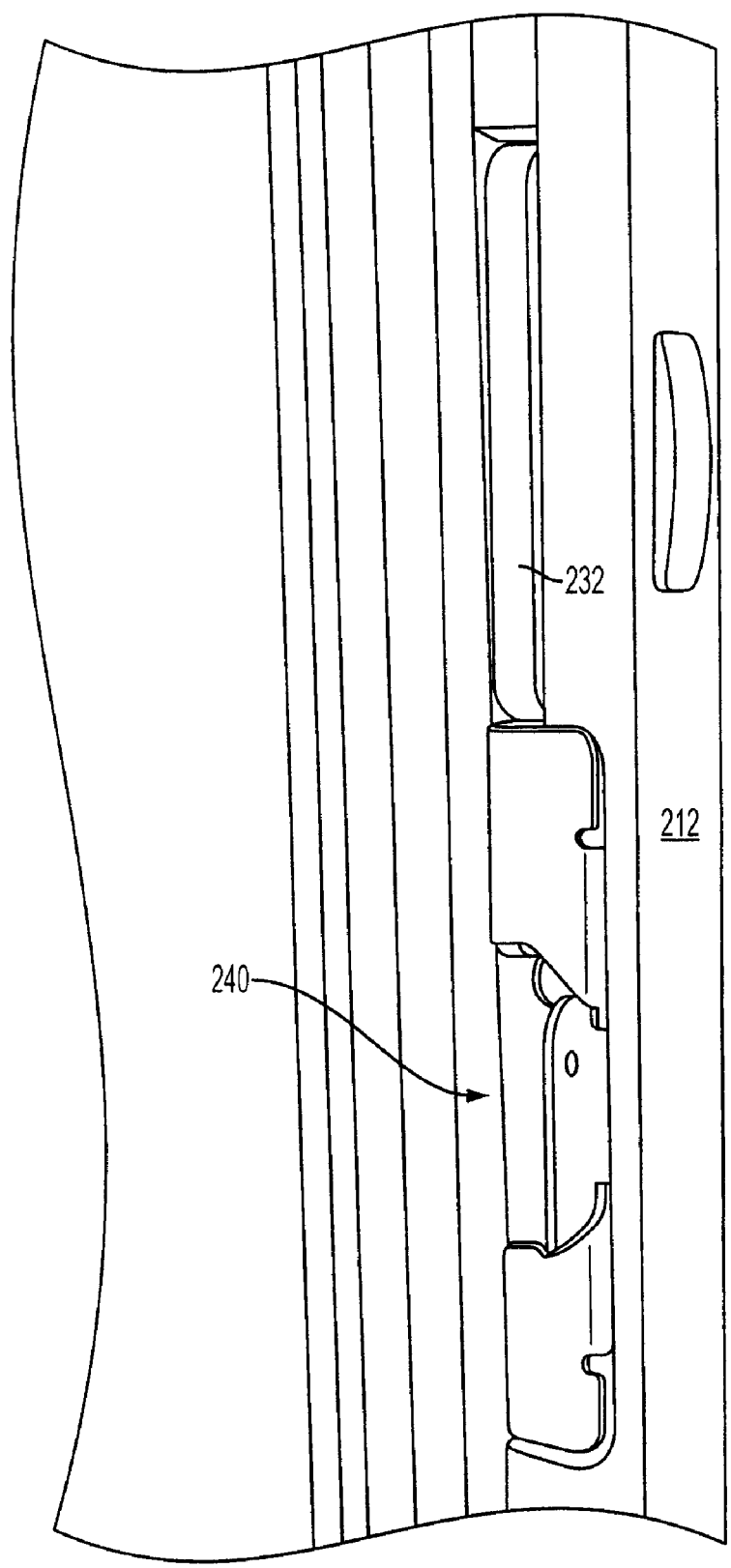
FIG. 7 shows the third embodiment installed in position in a fenestration unit.

FIG. 5 shows a partially deconstructed view of a status monitoring device of a third embodiment in a rail of a fenestration unit adjacent a sliding-type latch with an integrated magnet. Such sliding-type latches are common in casement windows. FIG. 6 shows the third embodiment of the status monitoring device of FIG. 5 with the latch in position on the rail. As shown in FIGS. 5 and 6, rail 212 is routed or otherwise formed with latch base receiving space 211 and with latch receiving space 213, which are sized to receive latch base 240 and latch 245. Latch 245, when operated to latch or unlatch a window, moves magnet 296 toward or away form reed switch 235 within cover 232, activating or deactivating the reed switch as an indication that latch 245 is properly seated, indicating the fenestration unit is secured in a locked position, or is not properly seated, indicating the fenestration unit is not secured in a locked position. Circuit board 280 detects activation or deactivation of reed switch 235, determines the condition of the latch based thereon and transmits the condition to a remote receiver that cooperates with magnetically operated reed switch 235 to transmit the position of latch 245. As shown in FIGS. 5 and 6, circuit board 280 is contained within a cover 232 disposed adjacent the latch base 240 in space 211. FIG. 7 shows the third embodiment installed in position in a fenestration unit. As shown in FIG. 7, the rail 212 is turned over from the position shown in FIGS. 5 and 6, which results in the lock 240 and the cover 232 housing the circuit board being disposed on the outermost side of the rail 212.

Figure 8:
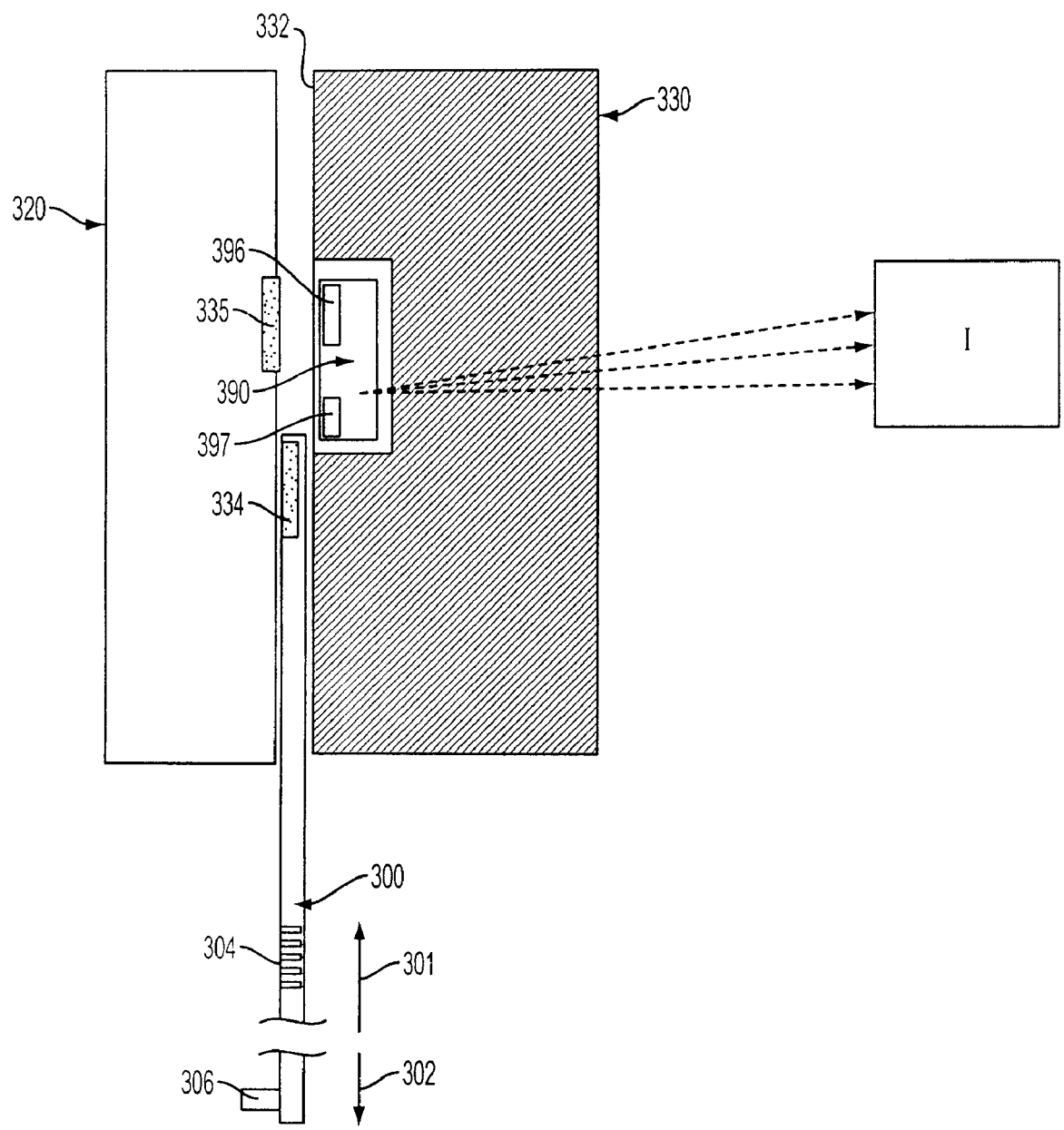
FIG. 8 shows a cut-away view of a status monitoring device of a fourth embodiment for a slide bar latch.

A status monitoring device can also be used with other types of locks and latches, such as a slide bar as shown in FIG. 8. In FIG. 8, slide bar 300 is slidably attached to jamb 330, so that it is able to slide longitudinally upwardly in direction 301, and downwardly in direction 302. Slide bar 300 is equipped with coupling features for coupling to one or more locking devices and for coupling to a central operator which enables the user to slide the slide bar up and down. In the particular embodiment of FIG. 8, moving bar 300 upward moves the locks coupled to it to the locked position, and sliding it downward unlocks the locks. The slide bar can be used to operate only one lock, or it can operate two or more locks simultaneously, depending upon how many locks are coupled to the slide bar. Several methods of coupling locks and operating mechanisms to the slide bar are known. Referring to FIG. 8, for example, openings 304 are provided for engaging the teeth of gear that operates a lock, in a rack and pinion manner. Peg 306, which may provide a coupling to a lock or to an operating mechanism, is adapted to engage a cam or a pivoting lever. Slide bar locking mechanisms are commonly used to operate more than one lock simultaneously. Such locking systems are commonly called multipoint locks, and can be found in casement and other hinged windows, as well as in patio and storm doors.

Referring again to FIG. 8, monitor 390 is located adjacent to edge 332 of jamb 330. Monitor 390 is equipped with magnetic reed switches 396 and 397. Slide bar 300 is equipped with magnet 334. When slide bar 300 is moved upwardly, to the locking position, magnet 334 is brought into close proximity to magnetically operated reed switch 397, thereby activating it to produce an indication that the slide bar is in the locking position. In a similar manner, panel 320, which may be a door or window panel, is equipped with magnet 335. When panel 320 is moved to the closed position, magnet 335 is brought into close proximity to magnetically operated reed switch 396, thereby activating it as an indication that panel 320 is in the closed position. Monitor 390 electronically integrates the indications of lock status and panel closure status into an integrated status code I that is transmitted to a remote status code receiver.

In an alternative embodiment, magnetic reed switch 397 is replaced by a mechanical switch operated by the end of slide bar 300 making physical contact with it, thereby depressing an actuator portion and closing an associated switch.

Figure 9:
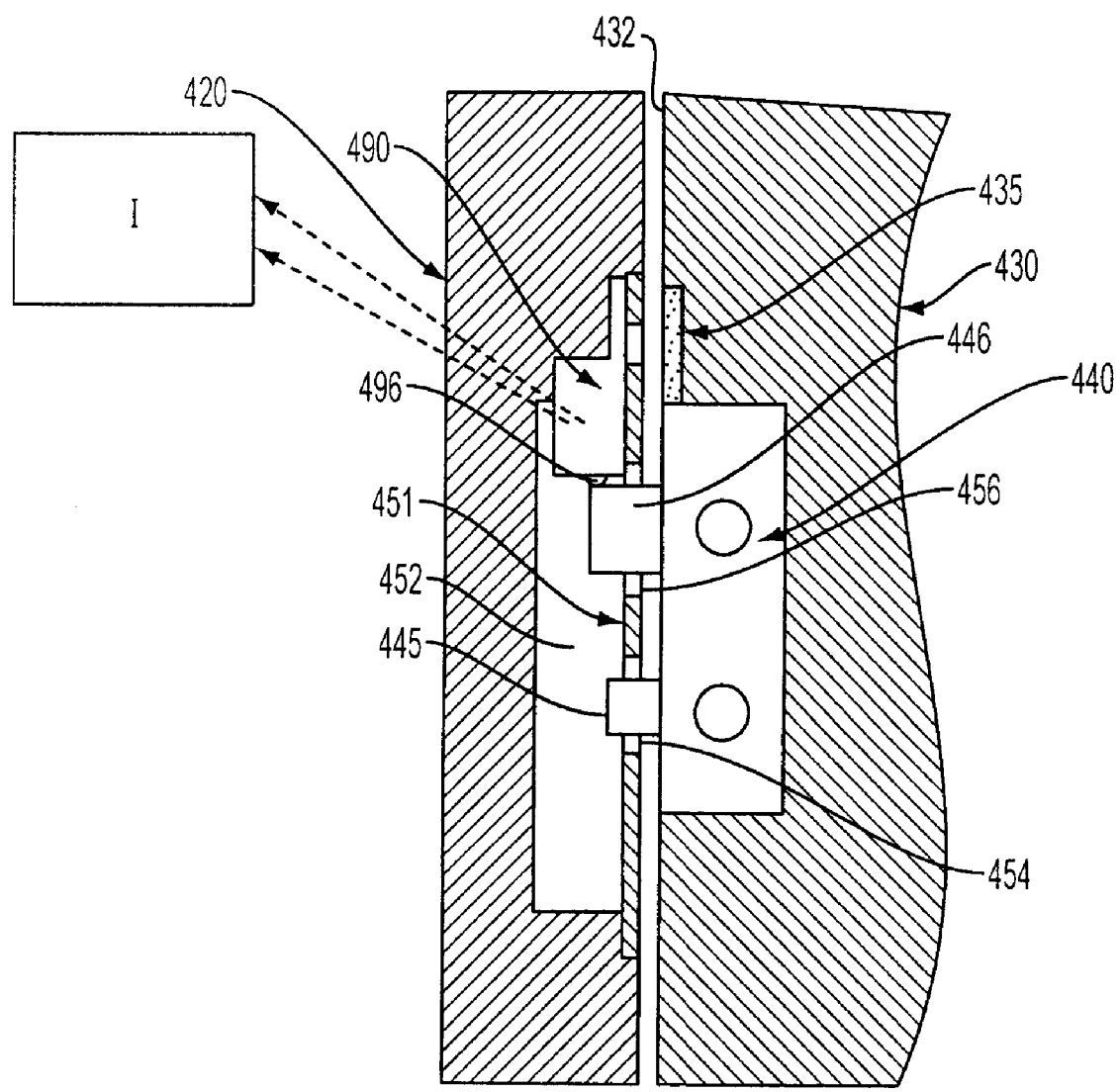
FIG. 9 shows a partial cut-away view of a status monitoring device of a fifth embodiment for a deadbolt latch.

FIG. 9 shows a partial cut-away view of a status monitoring device of a fifth embodiment for a deadbolt latch. In FIG. 9, a portion of a hinged closure panel 430, which may be a door panel, is shown in a closed position adjacent to vertical frame member, or jamb, 420. As used herein, the term closure panel will include doors, windows, and other like panels used in fenestration units. The panels may be hinged, sliding, or otherwise moveable. Closure panel 430 may be hinged to pivot about a vertical axis parallel to the page in FIG. 9. Lock 440 is provided in panel 430 for holding and locking panel 430 in its closed position relative to jamb 420. In this embodiment, lock 440 includes two locking members, latch 445, typically operated by a doorknob, handle, or other direct operating device, and deadbolt 446, which typically requires a key to operate. The key could be a conventional mechanical key or could be a card or other like device that operates locks by, for example, activating an electronic circuit or electromechanical device. Locking members 445 and 446 perform their locking function by engaging with apertures 454 and 456, respectively, in receiver plate 451, which is fixedly attached to jamb 420. Mortise 452 is provided in jamb 420 to provide space for locking members 445 and 446 to pass through receiver plate 451, in the conventional manner.

Figure 10:
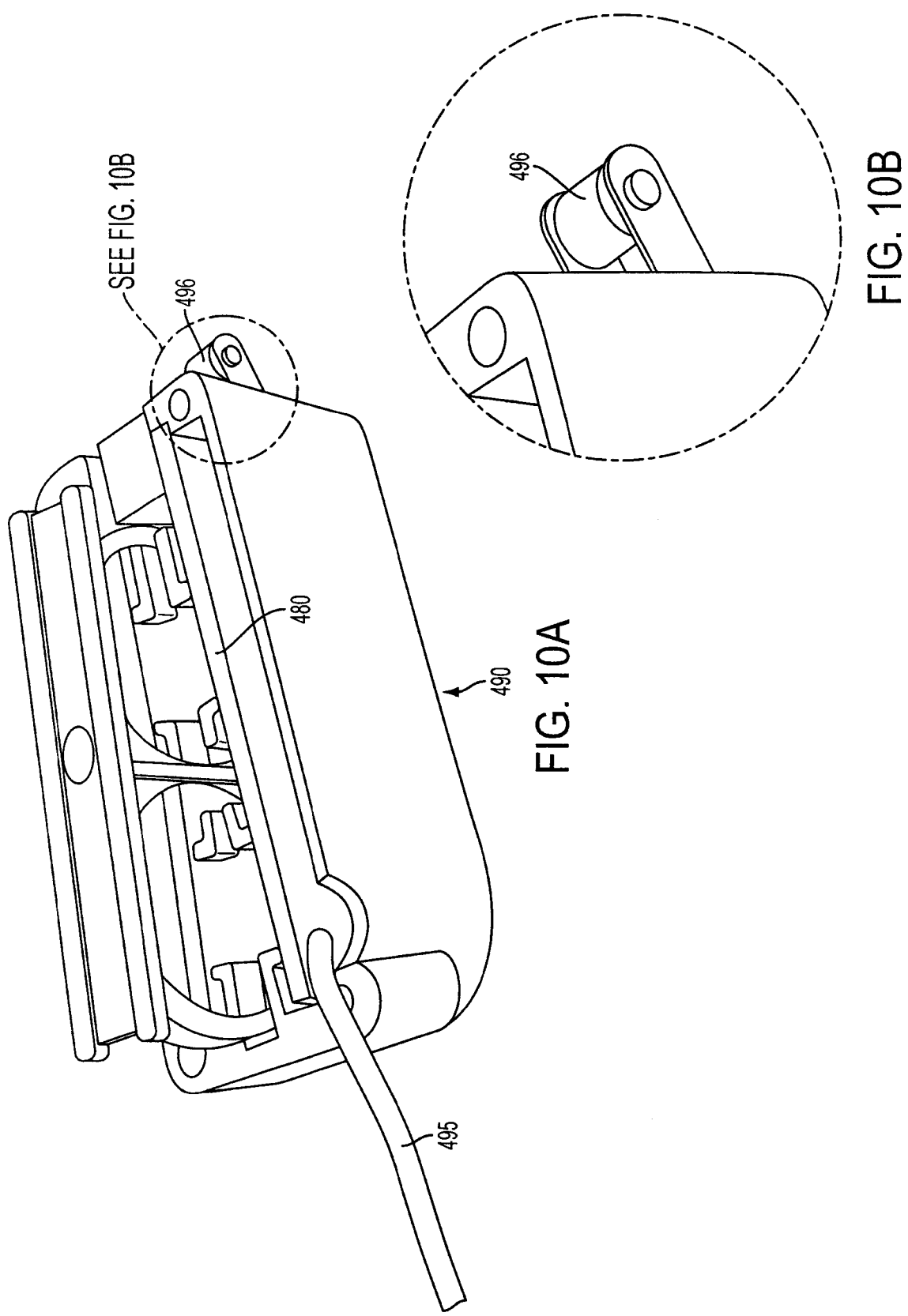
FIGS. 10A and 10B show the status monitoring device of the fifth embodiment.

In the embodiment portrayed in FIG. 9, closure status monitoring unit 490 is contained within mortise 452. In this embodiment, device 490 is held in place by a tab on receiver plate 451. Monitor device 490 is positioned proximate to deadbolt 446, as well as to edge 432 of panel 430. Unit 490 contains a position sensor that senses whether deadbolt 446 is in the extended, or locked, position, or whether it is in the retracted, or unlocked, position. One useful position sensor is a mechanical switch, having actuator 496, which is moved from an open circuit position to a closed circuit position or vice versa when deadbolt 446 is extended through aperture 456 in receiver plate 451. Also contained within unit 490 is a second sensor, for sensing the proximity of panel 430 to unit 490, which indicates whether panel 430 is open or closed. In this fifth embodiment, the second sensor is a magnetically actuated reed switch that moves from an open circuit position to a closed circuit position or vice versa when magnet 435 is brought into sufficiently close proximity to it, as would occur when panel 430 is in the closed position. As latch 445 extends its locked position with respect to receiver space 452, the deadbolt 446 engages switch 496 on monitor 490 to indicate a locked condition, which can be transmitted to an external source receiver via antennae 495. Alternatively though not shown, the mechanical switch 496 shown in FIGS. 9 and 10 can be replaced with an electronic switch not requiring physical contact with the latch 445 to indicate a locked condition. FIGS. 10A and 10B show close-up views of the status monitoring device of the fifth embodiment, showing circuit board 480 within monitor 490, and showing mechanical switch 496 extending from monitor 490.

Alternative embodiments can be formed in several variations. In particular, a lock position sensor can also be used to sense the position of latch 445. If the position of both latch 445 and deadbolt 446 are sensed, the lock status code would need to be expanded to describe the status of the locking members fully. Further, the physical configuration of unit 490 need not be limited to that shown in FIG. 9. The unit could, for example, be shaped to snap into the mortise without the use of a tab, could be configured to attach to plate 451 prior to installation of plate 451, or could be made up of two or more units that plug into one another to form a single unit. Further still, the monitoring unit can be made up of physically separate subunits, provided the subunits function in an electronically integrated manner. Also, sensors other than reed switches can be used, and when this is done, the circuitry for receiving the status signals and generating and transmitting the status codes will change accordingly.

Figure 11:
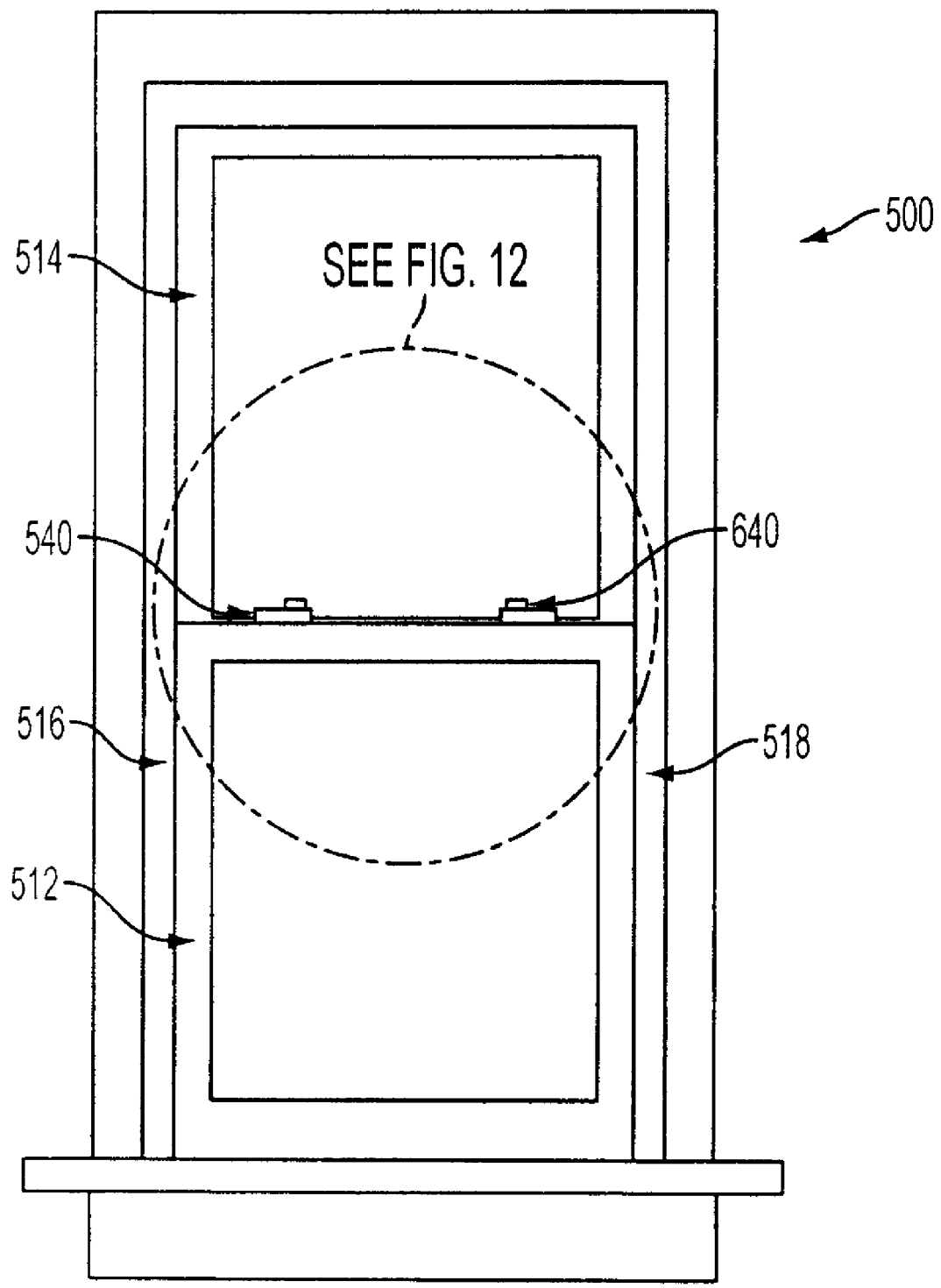
FIG. 11 shows a sixth embodiment of a status monitoring device for a multiple lock system.
Figure 12:
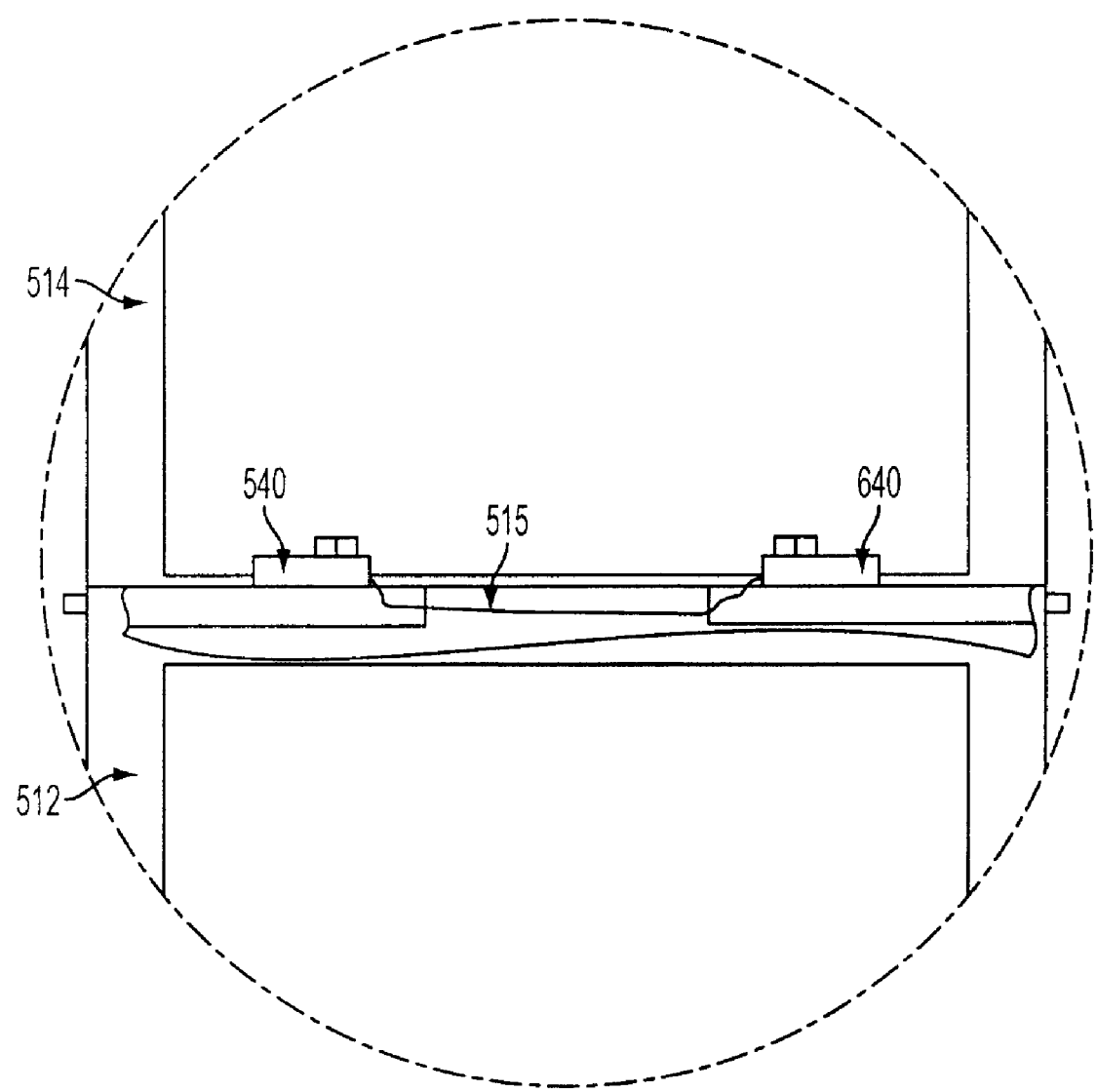
FIG. 12 shows cut-away view of the sixth embodiment.

The monitoring system can also be adapted to monitor the status of fenestration units having more than one lock. FIG. 11 shows a sixth embodiment of a status monitoring device for a multiple lock system. FIG. 12 shows cut-away view of the sixth embodiment. In FIGS. 11 and 12, window unit 500, viewed from the interior of a building structure, includes vertically sliding sashes 512 and 514. Sashes 512 and 514 can be secured by locking them together using latches 540 and 640, in the conventional manner. Latches 540 and 640 may further include tilt latches that engage jamb liners 516 and 518 and can be retracted to allow sash 512 to be tilted inward for cleaning or other maintenance purposes. A lock monitoring unit, as disclosed hereinabove, may be incorporated into latch 540 or 640, to monitor its status as being locked or unlocked. While monitoring of the status of lock 640 can be done by the use of a second monitoring unit, having its own code transmission capability, an alternative, and perhaps more cost effective, system is shown in FIG. 12. In FIG. 12, lock 640 is provided with a lock position sensor, which is connected, through transmission line 515 to the status monitoring device in lock 540, which then combines the status of lock 640 with that of lock 540 to produce an integrated signal portraying the overall status of both locks. Transmission line 515 can, for example, be simply a pair of wires connected to a position sensing switch in lock 640. Alternatively, transmission line 515 can be a pair of optical fibers, connected to a shutter, which is controlled by the position of lock 640. In yet another embodiment, the monitoring device in lock 540 can contain a light source directed toward lock 640, along with a light sensor, and lock 640 can be equipped with a reflective device that is moveable from a reflecting position to a non-reflecting position, wherein light from the light source is reflected back to the light sensor when lock 640 is in one position and not reflected when lock 640 is in another position. In this case, transmission line 515 may not be a solid transmission medium, but rather an open or transparent space through which light can be transmitted. Other modes of communication between locks 540 and 640 will be apparent to one skilled in the art. The open or closed position of sash 512 relative to 514 can be sensed by a magnet and a magnetic reed switch, in a manner similar to that portrayed in FIGS. 5-7. An expanded code can be calculated to portray the complete status of window 500, as shown in Table 1, in which a locked condition is represented by 1, an unlocked condition by 0, a closed position by 1, and an open position by 0. The code in Table 1 may be embedded in any suitable protocol, and may be encrypted for security or other purposes.

TABLE 1

| STATUS | CODE |
| --- | --- |
| Lock 540 unlocked, lock 640 unlocked, sash open | 000 |
| Lock 540 locked, lock 640 unlocked, sash open | 100 |
| Lock 540 unlocked, lock 640 locked, sash open | 010 |
| Lock 540 locked, lock 640 locked, sash open | 110 |
| Lock 540 unlocked, lock 640 unlocked, sash closed | 001 |
| Lock 540 locked, lock 640 unlocked, sash closed | 101 |
| Lock 540 locked, lock 640 locked, sash closed | 111 |
| Lock 540 unlocked, lock 640 locked, sash closed | 011 |

Figure 13:
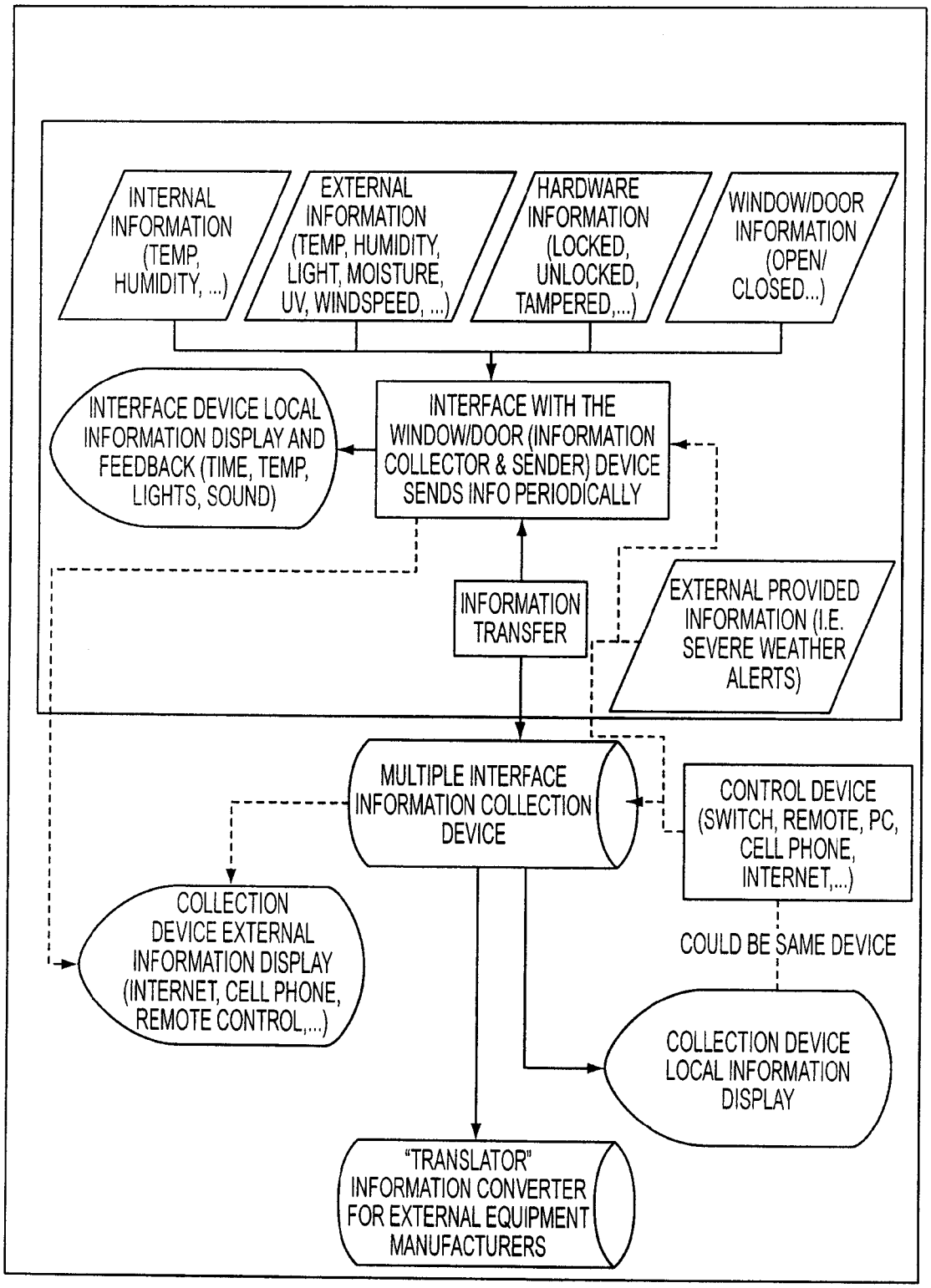
FIG. 13 shows a flow chart of information able to be collected by the status monitoring device of the invention and able to be transmitted to a remote command unit.

FIG. 13 shows a flow chart of information able to be collected by the status monitoring device of the invention and transmitted to a remote command unit. The device provides an interface to monitor the fenestration unit, or its environs, to which the device is attached or associated. The interface generally collects information and then either (1) stores such information, (2) triggers an alarm, light, or other display on the device itself, (3) transmits, either constantly or periodically, such information to a remote information receiving unit, or (4) a combination of these or other features. In one embodiment, the status monitoring device transmits information periodically to conserve battery life.

Figure 14:
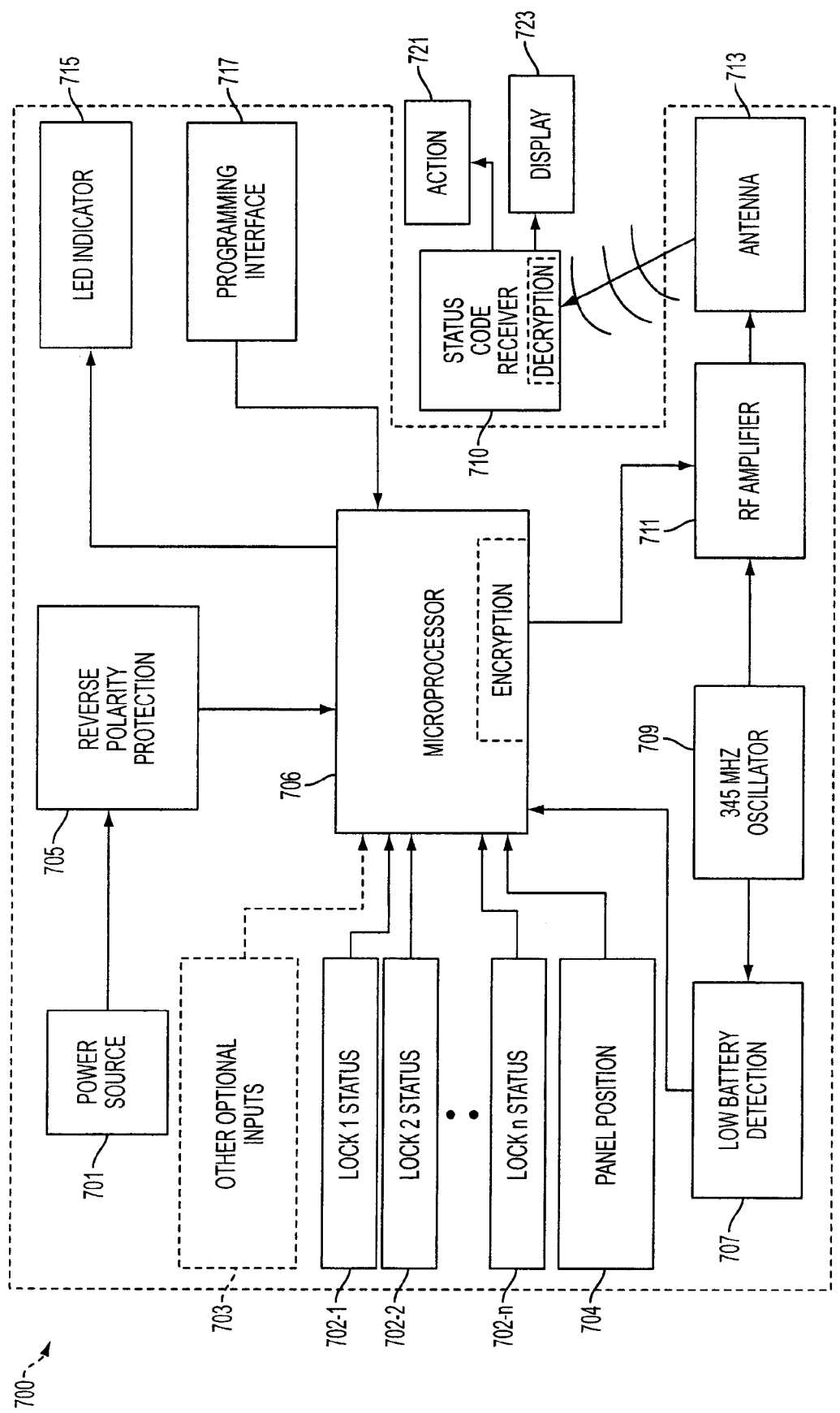
FIG. 14 shows a diagram of electronic components for an example status monitoring device.

Referring to FIG. 14, box 700 encompasses a functional diagram of electronic circuitry that may be contained within the monitor unit. Components performing the functions shown within box 700 may conveniently be located on a single circuit board, though other configurations are also possible. Generally, while the components performing the functions portrayed in FIG. 14 may not be physically integrated into a single unit, the components will be located in close proximity to one another and will function electronically as a single unit, transmitting a status code signal that integrates the information from all of the associated sensors into a single signal. A device that operates in this manner will be said to function in an electronically integrated manner. Alternative sensing devices that provide other optional inputs 703 may be provided, for example, as plug-in units that plug into a primary circuit board. Alternative sensing units may require that additional signal processing be provided in order for the overall device to function in an electronically integrated manner. FIG. 14 is exemplary of operation of a deadbolt latch, such as the one detailed in FIGS. 9-10 above.

Lock position sensor 702, which senses the position of deadbolt 62, can, as portrayed in FIGS. 9-10, be a mechanical switch actuated by contact with deadbolt 62. Alternatively, deadbolt position could be sensed by optical devices, sonic devices, RFID devices, or other suitable position sensing devices. Deadbolt 62 can be adapted for particular methods of sensing by providing it with reflective surfaces, RFID capability, or other suitable adaptations. Further, sensors for sensing lock conditions other than deadbolt position may also be provided.

Panel position sensor 704 can be a magnetically activated reed switch that is activated by magnet 435, contained in edge 432 of panel 430, as portrayed in FIG. 9. Plate 451 contains a third aperture to allow a portion of unit 490 to extend through it, thereby enhancing the magnetic coupling of magnet 435 with switch 704. The extension of unit 490 through plate 451 also allows access to unit 490 that may be needed, for example, for battery replacement. Other devices for sensing the position of panel 430 relative to jamb 420 may include binary devices that sense when panel 430 is sufficiently near to be considered closed, or sufficiently far to be considered open.

Microprocessor 706 is programmed to combine the signals from lock position sensor 702 and panel position sensor 704 to generate a code that describes or encodes the status of panel 430 and lock 440. The type of code used is not particularly limited, provided it fully describes the status of the panel and lock, and is understood by the code receiver. An example of a suitable code for a binary system, wherein the lock is either locked or unlocked, and the door is either open or closed, is shown in Table 2.

The code generated by code generator 706 is sent, possibly in encrypted form, to RF amplifier 711, which generates, in cooperation with oscillator 709, a signal that is sent to antenna 713 for transmission of the status code to the status code receiver 710. The receiver 710 can be located some distance from antenna 713, for example in another room of a house, or perhaps even in an adjacent building, such as a garage or other structure. If necessary, the status code receiver 710 can decrypt the transmission received from antenna 713.

In an alternative embodiment, rather than being programmed to integrate lock status and panel position status into a single code, code generator 706 generates and transmits separate codes for lock status and panel position, and sends each, along with codes to identify them as lock status or panel position, to the status code receiver 710, which integrates the codes into an appropriate overall status code.

TABLE 2

| STATUS | CODE |
| --- | --- |
| Lock unlocked, door open | 00 |
| Lock unlocked, door closed | 01 |
| Lock locked, door open | 10 |
| Lock locked, door closed | 11 |

It will be appreciated that the code shown in Table 2 can be further encoded to simplify the information presented to the user by sending a single open door code, namely 00, to the system to indicate that the door is open, whether locked or unlocked.

Status code receiver 710 receives the status code signal from antenna 713 and provides one or more suitable responses to the status code signals. Possible responses include outputs, such as an action 721 or display 723, to video displays, audio alarms, lighting devices, and other components of a security system. The status code shown in Table 2 need not be the exact protocol used in transmission. The code may be embedded in any suitable data transmission protocol, and can further be encrypted, for security or other reasons. Information beyond that shown in Table 2 may need to be transmitted, for example when a sensor is capable of sensing the specific degree to which a fenestration panel is open. When this is the case, an expanded code, along with the necessary electronic capability, can be created. Further, status code receiver 710 may be a stand alone unit or may be incorporated into a comprehensive security system.

The functions contained within box 700 in FIG. 14 generally will not require an outside power source, but will instead rely on an internal power source 701 such as a battery. In order to fit monitor 490 into a smaller space, it is useful for the battery to be as small as possible, thereby limiting the amount of power that such a battery would be able to deliver over an extended period of time. Several power saving features can be incorporated into the electronic functions of monitor 490. In particular, monitor 490 can be set only to transmit information when information needs to be transmitted. Generally, information is transmitted in packets, with three different types of information packets sent, namely registration packets, event packets, and supervisory packets. A battery may last months or years under such conditions. Additionally, other power sources, such as piezoelectric devices and other energy harvesting systems may be incorporated into the monitoring device, either alone or in combination with more conventional sources, such as batteries.

A registration data packet is transmitted upon installation of a battery in monitor 490. The registration data packet contains a code identifying the source of the registration data packet as being monitor 490. When monitor 490 is first installed, the programming interface can be used to enter information concerning the location of monitor 490, a description of the window or door in which it is installed, and other like information, in a manner that matches the entered information with the identification code for monitor 490. Upon replacement of a battery, the registration information is retransmitted. Optionally, other information, such as the date and time of battery replacement, may be recorded by the status code receiver, for convenience in maintaining maintenance records.

A second type of packet is an event packet, which is sent when an event such as locking or unlocking a lock, or opening or closing a panel, occurs. Inconsistencies between the lock status and panel status can be interpreted by the status code receiver as events requiring attention. Depending on the types of sensors installed in monitor 490, other event codes representing, for example, glass breakage, sudden acceleration of the panel, temperature, or other evidence of an event requiring attention, can also be contained in the packet. Battery power is conserved by transmitting an event packet only when an event occurs.

Another type of packet is the supervisory information packet, which is sent at set time periods to inform the status code receiver that monitor 490 is still operating. Failure to receive a supervisory packet within a prescribed time causes the receiver to generate an alarm signal. Possible causes for failure to receive a supervisory signal might include such things as broken electrical connections, a dead battery, and obstruction of the signal coming from antenna 713. Other battery saving strategies can also be employed, such as choosing an optimal voltage ramp-up profile just prior to beginning transmission.

Despite all efforts at power conservation, batteries will eventually approach failure, whether due to power consumption or simply due to the battery shelf life being exceeded. Useful features in circuitry include reverse polarity protection 705 to protect against incorrect battery insertion, an LED indicator 715 for diagnostics and installation troubleshooting purposes, and an accessible programming interface 717 to upgrade the code or software on transmitter post installation. In order to avoid loss of the monitoring function, it is useful to be able to detect deteriorating battery performance before actual failure. One measure of battery condition is the drop in output voltage when output current increases. Since a significant amount of current is drawn when a signal is being transmitted, one measure of battery condition is the voltage supplied to the signal transmitting function, in particular oscillator 709. Low battery detection device 707 monitors this voltage during transmission and compares it to the voltage between transmissions to determine the condition of the battery on an ongoing basis. If the battery is approaching failure, detection device 707 sends a signal to microprocessor 706, which creates an appropriate code to send to the status code receiver.

The device can display information on the device itself, such as by displaying time or temperature, can include a light, such as a Light-Emitting Diode (LED) that switches from green, e.g. when a lock is unlocked, to red when fully locked, or can provide an alarm to indicate a triggering event, such as the unlocking of a locked window. The device can monitor, collect, and display internal information inside a building and/or can monitor, collect, and display external information, such as external temperature, humidity, light, moisture, ultraviolet light, wind speed, etc. Further, the device can monitor, collect, and display hardware information, such as whether a lock is being or has been tampered with, or whether a lock is in a locked or unlocked condition. Further still, the present device can provide information about the fenestration unit to which it is attached or associated, such as whether a window or door is open or closed.

Once information is collected by the device, generally by or through the status code receiver, the information can be transferred to an information collection unit, which generally is remote from the device. In one embodiment, the device transmits the information wirelessly, such as via radio waves, microwave, Bluetooth, or other wireless transmission protocol, to the information collection unit (status code receiver). In another embodiment, the device may be directly or hard wired to the information collection unit. Additionally, the device can receive externally provided information, such as from the information collection unit or other unit, which can transmit information to the device in an embodiment which allows the device to receive information, such as severe weather alerts. The device in such embodiment can then respond accordingly, such as by displaying a warning light or an audible sound to apprise building occupants of such severe weather alerts or other condition.

The information collection unit can receive information from more than one status monitoring device. Generally, once information is transferred from a device to the information collection unit, the information collection unit can further manipulate or otherwise utilize the information, such as store information from the monitoring device(s), display warnings identifying which information collection devices are signaling or have signaled a specified event to warn a building occupant that an event has occurred. Information such as movement of a window or door from a set position as detected with an accelerometer, that the external humidity has increased or decreased, that it is raining outside, etc. can be relayed from the monitoring device to the information collection unit. The information from the monitoring device can be transmitted and displayed by the information collection device to an internet website, a cell phone, a Personal Digital Assistant (PDA), remote control, or some other system capable of displaying such information. The information collection device can be controlled externally by a switch, remote, computer, cell phone, PDA, internet, or any external manipulation device that can be used to control, display, notify, store, or otherwise use information. Additionally, such information can be transmitted to a monitoring company, such as an alarm company, to protect a building or building's occupants, such as by contacting the police, fire, or other authorities, or the building's occupants of a triggering event.

There are at least four general scenarios for providing information wirelessly from the present status monitoring device. In scenario 1, the status monitoring device provides local awareness via an alarm, visual light indicator, or other local device to inform building occupants about the lock, fenestration unit, or their environs. For example, the status monitoring device can indicate whether the window is open or closed, whether the lock is locked or unlocked, information about the internal or external environment, and transmit information to a central information receiving unit. The status monitoring device will allow monitoring of several events and trigger an alarm or light to warn that such event has occurred, such as activating an alarm if a lock or window is forced open, the indicator light can glow green if the lock is unlocked and glow red if the lock is locked, or the indicator light can blink if an alarm is armed. The sensor can be mounted into the strike of the lock to monitor proximity of the lock and enable a user to identify by immediate visual inspection of the light on the front of the lock whether the lock is fully engaged, locked, or unlocked. Further still, scenario 1 shows that the status monitoring device can include a built-in transmitter to transmit the lock status or information about the fenestration unit or its environs to a remote receiver, such as a tabletop or wall mounted receiver device. In scenario 2, a window monitor can receive a signal from at least one status monitoring device to show the window or lock status or information collected by the device's sensors. In scenario 3, a security system can receive the signal from the device(s); such security system can be a brand name security system that can then use the information to notify a building occupant or authorities of a triggering event. In scenario 4, the ability to monitor the device(s) anywhere via cell phone, internet connection, PDA, or the like is provided.

The status monitoring device can include additional features, such as an accelerometer or displacement or position sensor (hereinafter "accelerometer"). Such accelerometer or displacement or position sensor can capture or detect whether a window sash or door panel has changed position, such as from a sudden movement of the window or door. For example, a window can be set in a venting position and an alarm armed (this would provide secure venting). If the sash is then moved from the set venting position, an accelerometer can detect such sash movement and provide information of the occurrence of such event. An accelerometer can also detect impact or jarring of a window or door, which can be the result of a forced entry, an extreme weather condition, or a child trying to open the window. An accelerometer can also detect rotation of a window sash or a door panel. The position change or displacement of a window or a door can also be detected using several other sensing devices in lieu of an accelerometer, such as optical sensors, capacitance sensors, pressure sensors, Hall Effect sensors, encoder wheels, and potentiometers (resistors) or the like.

The device of this invention utilizes the hardware components of a window or door as an interface to obtain information. Some examples of hardware components that correspond to specific window types and examples of information that such hardware components can provide include, but are not limited to, the following:

Hung Windows (Double Hung and Single Hung):
Locks—Information of the locked/unlocked status
Keepers—Information on the open/closed status, locked/unlocked status
Tilt Latches—Position detection, open/closed status
Pivot Pins—Position detection, open/closed status
Sash Balance System—Information on the system
Gliding Window and Doors:
Locks—Information of the locked or unlocked status
Keepers (baskets)—Information on the open/closed status, locked/unlocked status
Glide Wheels or Glide Pins—Position detection, open/closed status
Casement/Awning Window:
Operators—Sense human contact, information on the open/closed status
Hinges—Information on the open/closed status
Locks—Information of the locked/unlocked status, impact sensing.
Keepers—Information of the locked/unlocked status, impact sensing
Hinge Doors
Hinges—Position detection, open/closed status
Locks and deadbolts—Open/closed status, locked/unlocked status
Handles—Open/closed status, locked/unlocked status, sensing human contact
Keepers (baskets)—Open/closed status, locked/unlocked status
Multipoint Locks—Locked/unlocked status, impact sensing The invention has been described in terms of preferred configurations and methodologies considered by the inventors to be the best mode of carrying out the invention. These preferred embodiments are presented as examples only and should not be construed as limiting the scope of the invention. A wide variety of additions, deletions, and modifications to the illustrated and described embodiments might be made by those of skill in the art without departing from the spirit and scope of the invention.

We claim:

1. A status monitoring device for a window or door, the window or door including at least one panel movable between an open panel position and a closed panel position, and the window or door including at least one latch movable between a locked position and an unlocked position, the device comprising:
a first sensor that detects whether the at least one panel is in the open panel position or the closed panel position;
a second sensor that detects whether the at least one latch is in the locked position or the unlocked position; and,
a code generator that generates codes; the codes including a latch status code separate from a panel status code; the latch status code indicating the detected position of the latch and the panel status code indicating the detected position of the panel.

2. The device of claim 1 wherein the device transmits a first signal when the latch is in the locked position and transmits a second signal when the latch is in the unlocked position.

3. The device of claim 1 further including an output from an indicator.

4. The device of claim 3 wherein the output comprises one or more of visible light, display, audible signal, wireless transmission, or wired transmission.

5. The device of claim 1 further including a code transmitter for transmitting the codes generated by the code generator.

6. The device of claim 1 wherein the first sensor comprises at least one of a reed switch, a mechanically operated switch, a mechanical switch, an acoustical sensor, an RFID device, or an optical sensor.

7. The device of claim 1 wherein the second sensor comprises at least one of a reed switch, a mechanically operated switch, a mechanical switch, an acoustical sensor, RFID device, or an optical sensor.

8. The device of claim 1 wherein the device is operable to gather information about environmental conditions surrounding the window or door, with the information comprising at least one of outside temperature, inside temperature, humidity, moisture, light, or motion.

9. The device of claim 8 wherein the device is operable to gather a time of a change of information about the window or door.

10. The device of claim 9 wherein the information comprises at least one of the time of the change in position of the at least one movable panel of the window or door, the time of the change in position of the at least one latch of the window or door, the time of the change of at least one interior environmental condition, or the time of the change of at least one exterior environmental condition.

11. The device of claim 1 further comprising a battery in a battery carrier that is movable from a position interior the device to a position exterior the device.

12. The device of claim 1 wherein the movement of the at least one panel is toward the closed position.

13. The device of claim 1 wherein the code generator is located remote from the monitoring device.

14. The device of claim 1 wherein the first sensor detects whether the latch is in the locked position or the unlocked position independent of the position of the at least one panel.

15. The device of claim 1 wherein the codes generated define a set of four possible states: (1) open and unlocked, (2) open and locked, (3) closed and unlocked, or (4) closed and locked.

16. The device of claim 1 wherein the codes generated are encoded to define a set of three possible states: (1) open, (2) closed and unlocked, or (3) closed and locked.

17. The device of claim 1 wherein the codes generated are transmitted to a status code receiver.

18. The device of claim 1 wherein the codes generated are transmitted wirelessly to a status code receiver.

19. The device of claim 1 further comprising a visual display.

20. The device of claim 1 further comprising an audio output.

21. The device of claim 1 wherein the device transmits a first signal when the panel is in the open panel position and transmits a second signal when the panel is in the closed panel position.

22. A status monitoring device for a window or door that includes at least one slidable panel movable between an open position and a closed position, the device comprising:
   a latch coupled to a base, the base being attached to the at least one slidable panel;
   a keeper;
   the latch engaging the keeper when the at least one slidable panel is in the closed position;
   a first sensor that detects whether the panel is in the open position or the closed position;
   a second sensor that detects whether the latch is in a locked position or an unlocked position; and;
   a transmitter for transmitting the detected position of the latch with respect to the base independent of the detected position of the at least one slidable panel.

23. The device of claim 22 wherein the second sensor comprises at least one of a reed switch, a mechanically operated switch, a mechanical switch, an acoustical sensor, RFID device, or an optical sensor.

24. The device of claim 22 further comprising an output from an indicator.

25. The device of claim 24 wherein the output comprises one or more of visible light, display, or audible signal.

26. The device of claim 22 wherein the device is operable to gather information about environmental conditions surrounding the window, with the information comprising at least one of outside temperature, inside temperature, humidity, moisture, light, or motion.

27. The device of claim 26 wherein the device is operable to gather a time of a change of information about the window.

28. The device of claim 27 wherein the information comprises at least one of the time of the change in position of the at least one slidable panel of the window or door, the time of the change position of the latch, the time of the change of at least one interior environmental condition, or the time of the change of at least one exterior environmental condition.

29. A status monitoring device for a closure assembly, the closure assembly including at least one panel movable between an open position and a closed position, the closure assembly further comprising a locking assembly, the locking assembly comprising: at least one latch located on the at least one panel, an operator assembly located on the at least one panel, and a coupling member operatively connecting the at least one latch with the operator assembly; the monitoring device comprising:
   a first sensor for detecting the position of the panel;
   a second sensor for detecting the position of a moving element of the locking assembly;
   a code generator for generating codes defining the panel position and the moving element position; and,
   a code transmitter for transmitting the generated codes to a code receiver.

30. The device of claim 29 further comprising an output from an indicator.

31. The device of claim 30 wherein the output comprises one or more of visible light, display, audible signal, wireless transmission, or wired transmission.

32. The device of claim 29 wherein the latch position sensor comprises at least one of a reed switch, a mechanically operated switch, an acoustical sensor, an RFID device, or an optical sensor.

33. The device of claim 29 wherein the panel position sensor comprises at least one of a reed switch, a mechanically operated switch, an acoustical sensor, or an optical sensor.

34. The device of claim 29 further comprising a battery in a battery carrier that is movable from a position interior the device to a position exterior the device.

35. The device of claim 29 wherein the device is operable to gather information about environmental conditions surrounding the closure assembly, with the information comprising at least one of outside temperature, inside temperature, humidity, moisture, light, or motion.

36. The device of claim 29 wherein the device is operable to gather a time of a change of information.

37. The device of claim 36 wherein the information comprises at least one of the time of the change in position of the closure assembly, the time of the change position of the latch, the time of the change of at least one interior environmental condition, or the time of the change of at least one exterior environmental condition.

38. The device of claim 29 wherein the coupling member is remotely connected to the at least one latch.

39. A hinged closure assembly comprising:
   a frame including a latch receiver;
   at least one panel disposed in the frame, the at least one panel being movable between a closed position and an open position;
   a latch having a locked position, for locking the at least one panel in the closed position, and an unlocked position; the latch including at least one movable element and a base; the movable element engaging the latch receiver in the locked position;
   a first sensor detecting when the at least one panel is in the closed position and when the at least one panel is in the open position;
   a second sensor detecting when the movable element is in the locked position relative to the base and when the movable element is in the unlocked position relative to the lock assembly; and, a processor coupled to the first sensor and the second sensor, the processor programmed to determine a status of the closure assembly based at least on the detections of the sensors.

40. The closure assembly of claim 39 further comprising a transmitter for transmitting the status of the window or door.

41. The closure assembly of claim 39 wherein at least one of the first and second sensors comprises at least one of a reed switch, a mechanically operated switch, a mechanical switch, an acoustical sensor, RFID device, or an optical sensor.

42. The closure assembly of claim 39 wherein the first sensor indicates movement of the at least one panel.

43. The closure assembly of claim 42 further comprising an output from an indicator.

44. The closure assembly of claim 43 wherein the output comprises one or more of visible light, display, audible signal, wireless transmission, or wired transmission.

45. The closure assembly of claim 39 wherein the window or door is operable to gather information about environmental conditions surrounding the window or door, with the information comprising at least one of outside temperature, inside temperature, humidity, moisture, light, or motion.

46. The closure assembly of claim 45 wherein the closure assembly is operable to gather a time of a change of information.

47. The closure assembly of claim 46 wherein the information comprises at least one of the time of the change in position of the at least one panel, the time of the change position of the latch, the time of the change of at least one interior environmental condition, or the time of the change of at least one exterior environmental condition.

48. A status monitoring device for a closure assembly, wherein the closure assembly comprises a fixed frame and at least one panel movable between a closed position and an open position, the device comprising:
a latch movable from a locked position to an unlocked position;
a latch position sensor;
a panel position sensor;
a microprocessor; and,
a code transmitter;
wherein the latch position sensor senses the position of the latch, wherein the panel position sensor senses the position of the panel, and wherein a combination of the panel position sensor, the latch position sensor, the microprocessor, and the status code transmitter operate in an electronically integrated manner; and wherein the device is positioned to sense both the position of the latch and the position of the at least one panel; and wherein the microprocessor generates a status code that integrates the latch position with the panel position.

49. The device of claim 48 further comprising an output from an indicator.

50. The device of claim 48 wherein the output comprises one or more of visible light, display, audible signal, wireless transmission, or wired transmission.

51. The device of claim 48 wherein the latch position sensor comprises at least one of a reed switch, a mechanically operated switch, a mechanical switch, an acoustical sensor, RFID device, or an optical sensor.

52. The device of claim 48 wherein the panel position sensor comprises at least one of a reed switch, a mechanically operated switch, a mechanical switch, an acoustical sensor, an RFID device, or an optical sensor.

53. The device of claim 48 further comprising a battery in a battery carrier that is movable from a position interior the device to a position exterior the device.

54. The device of claim 48 wherein the device is operable to gather information about environmental conditions surrounding the closure assembly, with the information comprising at least one of outside temperature, inside temperature, humidity, moisture, light, or motion.

55. The device of claim 54 wherein the device is operable to gather a time of a change of information.

56. The device of claim 55 wherein the information comprises at least one of the time of the change in position of the at least one panel, the time of the change of position of the latch, the time of the change of at least one interior environmental condition, or the time of the change of at least one exterior environmental condition.

57. A lock assembly for a window or door comprising:
an elongate longitudinally sliding member oriented generally parallel to an edge of a window or door panel and translating in a direction generally parallel to the edge of the window or door panel;
a latch operated by the sliding member for locking a window or door panel;
an operator that slides the elongate member to move the latch between unlocked and locked positions;
a first sensor for detecting, independent of sliding member position, whether the panel is in an open or closed position;
a second sensor for detecting, independent of panel position, whether the latch is in the unlocked or locked position; and
a code generator for generating codes defining a status of the window or door, wherein the codes define the status as being one of the following:
panel open, latch unlocked;
panel open, latch locked;
panel closed, latch unlocked; or
panel closed, latch locked.

58. The lock assembly of claim 57 wherein the second sensor comprises at least one of a reed switch, a mechanically operated switch, a mechanical switch, an acoustical sensor, RFID device, or an optical sensor.

59. The lock assembly of claim 57 wherein the first sensor comprises at least one of a reed switch, a mechanically operated switch, a mechanical switch, an acoustical sensor, RFID device, or an optical sensor.

60. The lock assembly of claim 57 wherein the output comprises one or more of visible light, display, audible signal, wireless transmission, or wired transmission.

61. The lock assembly of claim 57 wherein the assembly is attached to the sliding member.

62. The device of claim 5 wherein the device is operable to combine the latch position and panel position into a single code and transmit the code to a remote location.

63. The device of claim 62 wherein the device is operable to gather a time of a change of information.

64. A status monitoring device for a window or door, the window or door including at least one panel movable between an open panel position and a closed panel position, the device comprising:
a panel position detector for detecting whether the panel is in the open panel position or the closed panel position,
a lock assembly that at least includes a cam and a base;
wherein the cam engages a keeper when the lock is in a locked position;
a lock assembly position detector for detecting whether the lock assembly is in the locked position or the unlocked position;
wherein the monitoring device further includes a code generator that generates a first panel position status code indicating that the panel is in the open panel position and a second panel position status code indicating that the panel is in the closed panel position, and wherein the code generator further generates a first lock position status code indicating that lock assembly is in an unlocked position and a second lock position status code indicating that the lock assembly is in a locked position.

65. The device of claim 64 wherein the device further includes a code transmitter for transmitting the generated codes to a code receiver.

66. The device of claim 65 wherein the code transmitter is located within the device.

67. The device of claim 65 wherein the code receiver is located at a location remote from the code transmitter.

68. The device of claim 64 wherein the code transmitter transmits wirelessly.

69. The device of claim 64 further including a code integrator that integrates the panel position status code and the lock position status code into a combined set of codes.

70. The device of claim 69 wherein the combined set of codes includes codes indicating one of the following:
   a) the panel is in the opened position regardless of whether the lock assembly is in the locked or the unlocked position;
   b) the panel is in the closed position with the lock assembly in the unlocked position;
   c) the panel is in the closed position with the lock assembly in the closed position.

71. The device of claim 64 wherein the code generator is located within the device.

72. A status monitoring device for a window or door, the window or door including at least one panel movable relative to a fixed structure between an open panel position and a closed panel position, the device comprising:
   a first position sensor that detects the position of the panel relative to an activating portion of the fixed structure, wherein the first position sensor is fixedly attached to the panel;
   a second position sensor that detects the position of a movable element of a lock assembly, wherein the second position sensor and the lock assembly are each fixedly attached to the panel, and the movable element can be in a locked position or an unlocked position;
   a code generator that generates codes from the position of the movable element of the lock and from the position of the panel to indicate whether the lock assembly is in a locked or an unlocked position and whether the panel is in an open or a closed position.

73. The device according to claim 72 wherein the codes are transmitted to a location remote from the panel.

74. The device according to claim 72 wherein the activating portion is a magnet.

75. The device according to claim 72 wherein the activating portion is an RFID device.

76. A status monitoring device for a window or door, the window or door including at least one panel movable relative to a fixed structure between an open panel position and a closed panel position, the device comprising:
   a first position sensor that detects the position of an activating portion of the panel relative the fixed structure, wherein the first position sensor is fixedly attached to the fixed structure;
   a second position sensor that detects the position of a movable element of a lock assembly, wherein the second position sensor and the lock assembly are each fixedly attached to the fixed structure, and the movable lock element can be in a locked position or an unlocked position;
   a code generator that generates codes from the position of the movable element of the lock assembly and from the position of the panel to indicate whether the lock assembly is in a locked or unlocked position and whether the panel is in an open or a closed position.

77. The device according to claim 76 wherein the codes are transmitted to a location remote from the fixed structure.

78. The device according to claim 76 wherein the activating portion is a magnet.

79. The device according to claim 76 wherein the activating portion is an RFID device.

80. A lock assembly for a first panel of a door or window slidable with respect to a second panel comprising:
   a base fixedly attached to the first panel;
   a latch movably attached to the base and movable between a locked position and an unlocked position;
   a keeper fixedly attached to the second panel and located such that the latch engages the keeper when the latch is in a locked position and the panel is in the closed position;
   a first sensor fixedly attached to the first panel for detecting the position of the first panel relative to the second panel independent of the lock position;
   a second sensor fixedly attached to the first panel for detecting whether the latch is in the locked or unlocked position independent of whether the first panel is in the open or closed position; and
   a code generator for generating codes defining a status of first panel, wherein the codes define the status as being one of the following:
   panel open, latch unlocked;
   panel open, latch locked;
   panel closed, latch unlocked; or
   panel closed, latch locked;
   wherein the second panel is movable between open and closed positions.

81. The lock assembly of claim 80 wherein the first sensor is fixedly attached to the first panel.

82. The lock assembly of claim 80 wherein the second sensor is fixedly attached to the first panel.

83. The lock assembly of claim 80 wherein the first sensor detects the panel position of the first panel relative to the second panel independent of the lock position.

84. The lock assembly of claim 80 wherein the second sensor detects whether the latch is in the locked or unlocked position independent of whether the first panel is in the open or closed position.

* * * * *